United States Patent
Pearce et al.

(10) Patent No.: US 7,731,651 B2
(45) Date of Patent: Jun. 8, 2010

(54) DEVICE TO DEPLOY A RESILIENT SLEEVE TO CONSTRICT ON BODY TISSUE

(75) Inventors: Joseph R. Pearce, Duvall, WA (US); David J. Reddy, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 1099 days.

(21) Appl. No.: 11/376,780

(22) Filed: Mar. 15, 2006

(65) Prior Publication Data

US 2006/0212046 A1 Sep. 21, 2006

Related U.S. Application Data

(60) Provisional application No. 60/662,942, filed on Mar. 17, 2005.

(51) Int. Cl.
*A61F 13/00* (2006.01)
(52) U.S. Cl. .......................................... 600/37; 606/140
(58) Field of Classification Search ............. 600/16–18, 600/37; 606/140; 623/8; 128/898
See application file for complete search history.

(56) References Cited

U.S. PATENT DOCUMENTS

| | | | |
|---|---|---|---|
| 5,972,002 A | 10/1999 | Bark et al. | |
| 6,514,290 B1 * | 2/2003 | Loomas | 623/23.65 |
| 6,790,172 B2 * | 9/2004 | Alferness et al. | 600/37 |
| 7,300,442 B2 * | 11/2007 | Cherfas et al. | 606/106 |
| 7,338,434 B1 * | 3/2008 | Haarstad et al. | 600/37 |
| 7,399,272 B2 * | 7/2008 | Kim et al. | 600/37 |

FOREIGN PATENT DOCUMENTS

| | | |
|---|---|---|
| DE | 92 05 453 U1 | 6/1992 |
| WO | WO 96/19145 | 6/1996 |
| WO | WO 03099141 A1 * | 12/2003 |

OTHER PUBLICATIONS

PCT Search Report and Written Opinion mailed Dec. 12, 2006.
PCT Search Report mailed Aug. 14, 2006.
PCT Preliminary Report on Patentability, and Written Opinion mailed Sep. 27, 2007 in related PCT application.

* cited by examiner

*Primary Examiner*—John P Lacyk
(74) *Attorney, Agent, or Firm*—Knobbe Martens Olson & Bear LLP

(57) ABSTRACT

The preferred embodiment of the invention contemplates a device configured to prepare and deploy a resilient sleeve on to a portion of body tissue. The device expands the resilient sleeve, uses a vacuum system to draw the body tissue in to the resilient sleeve, and releases the resilient sleeve from the expanded state so that it captures and constricts the body tissue.

29 Claims, 34 Drawing Sheets

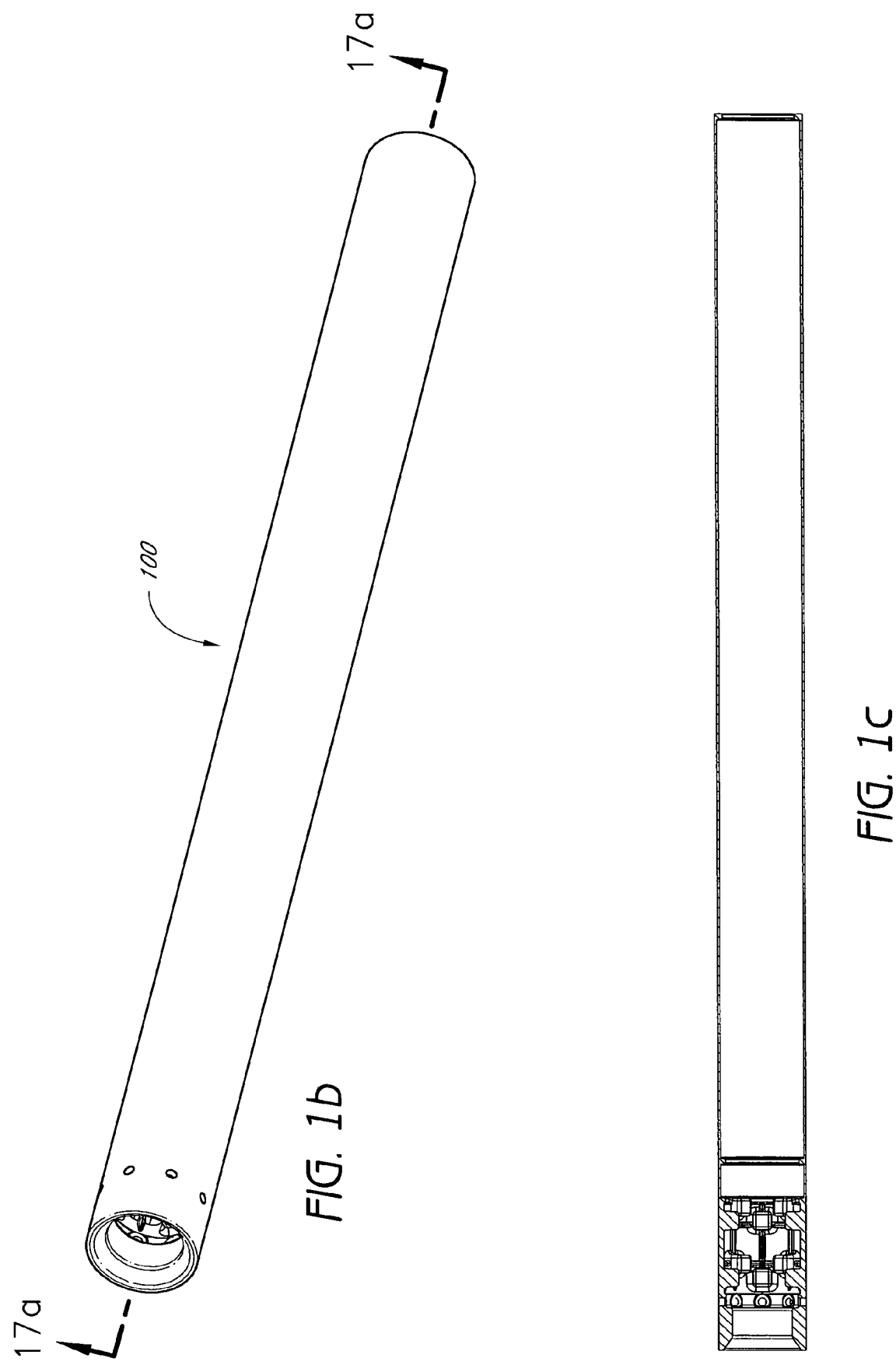

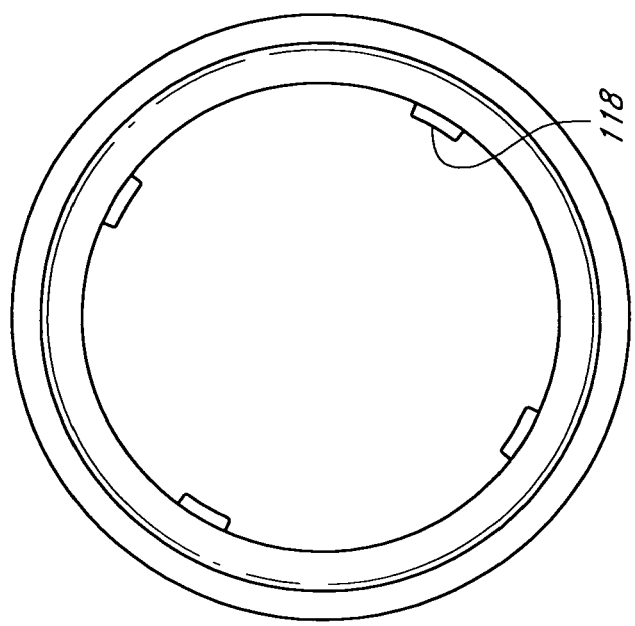
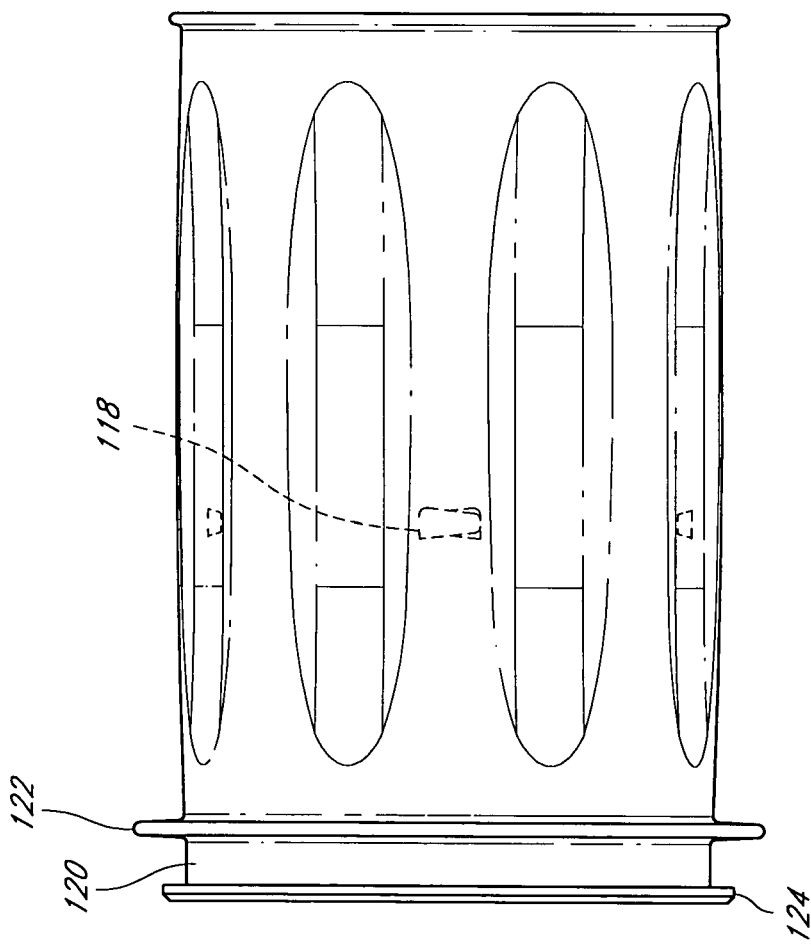
FIG. 4b
FIG. 4a

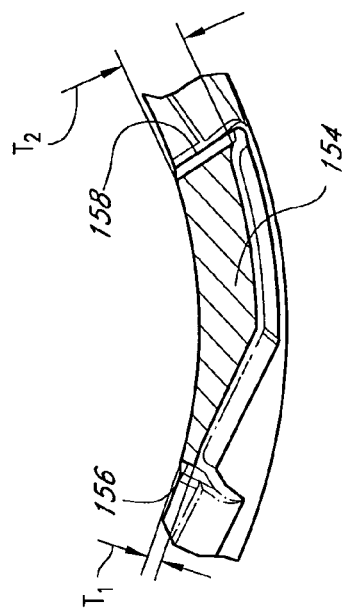
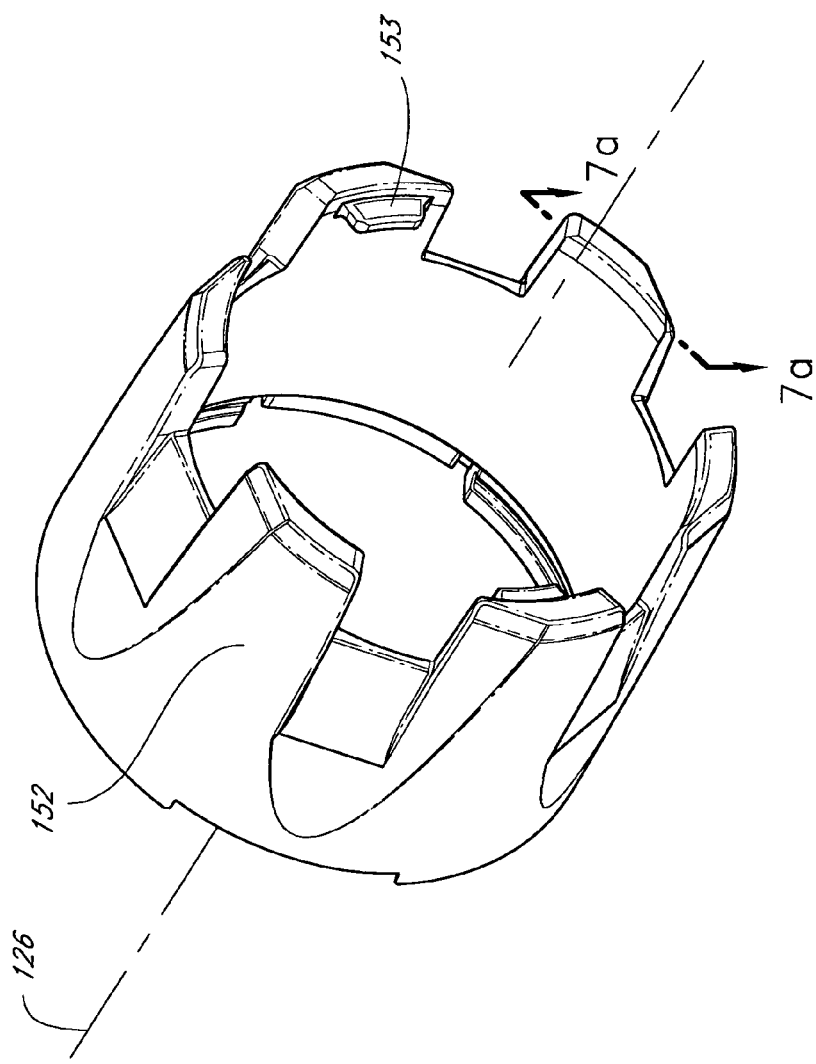
FIG. 7a
FIG. 7

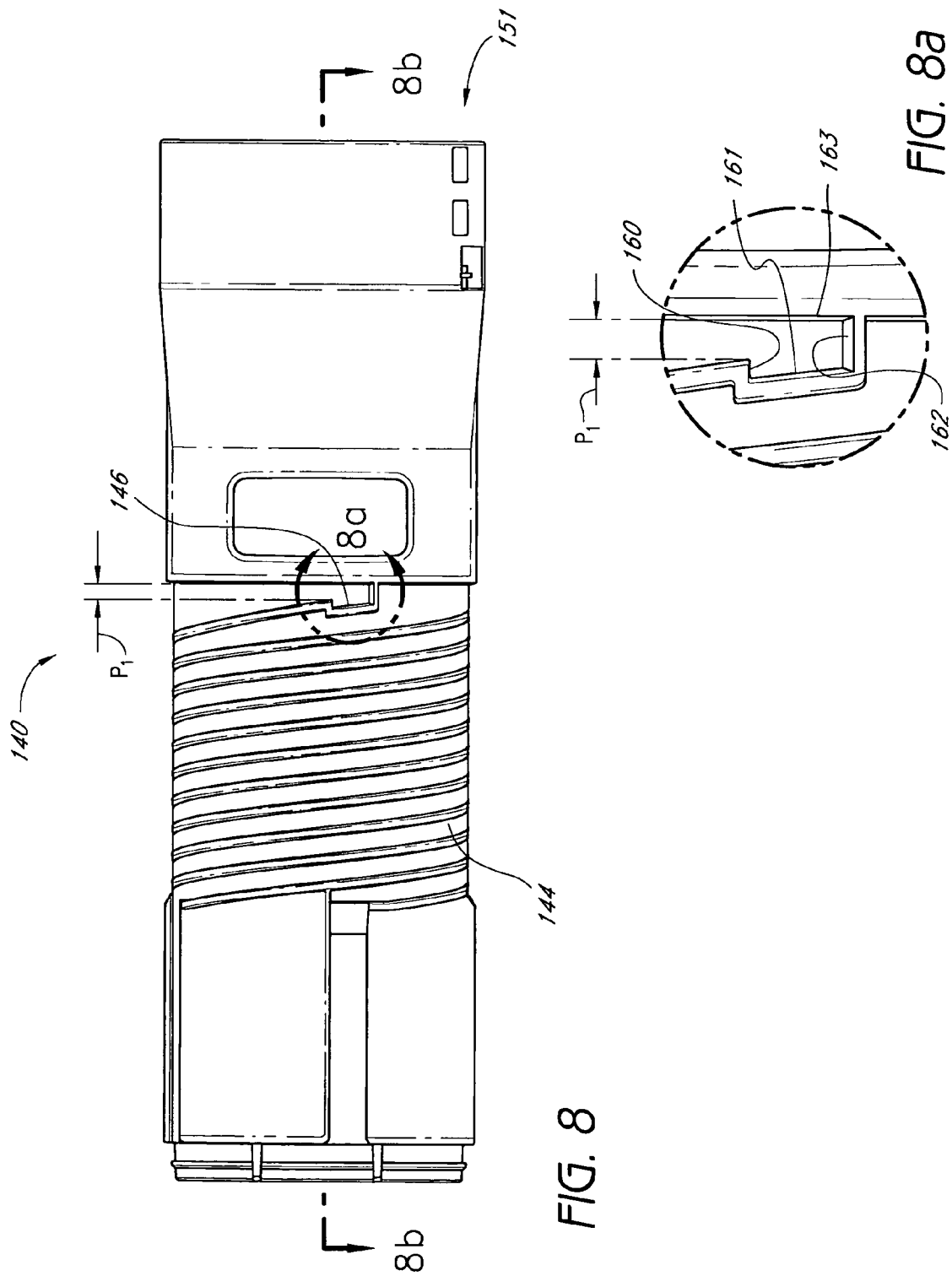

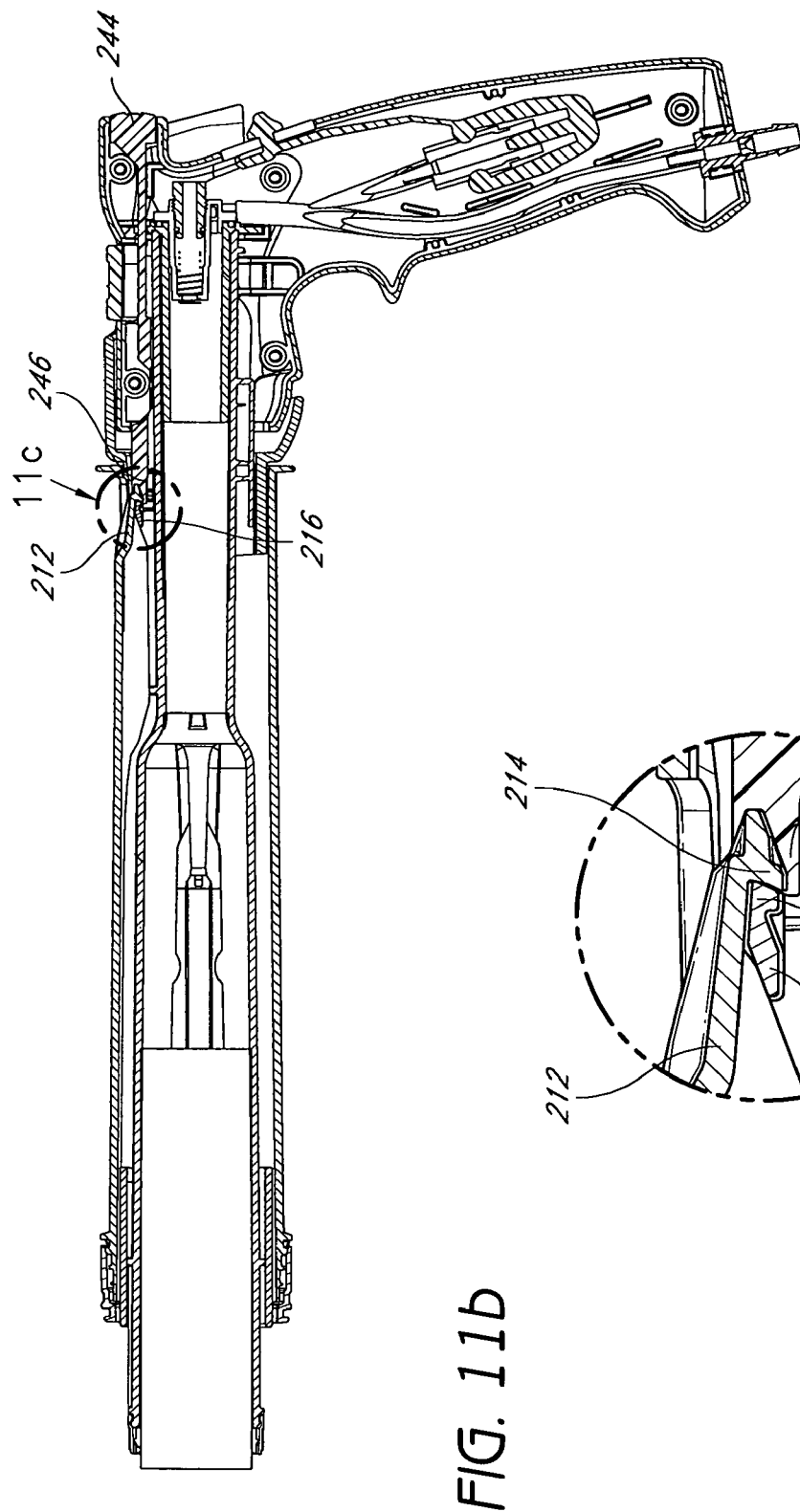
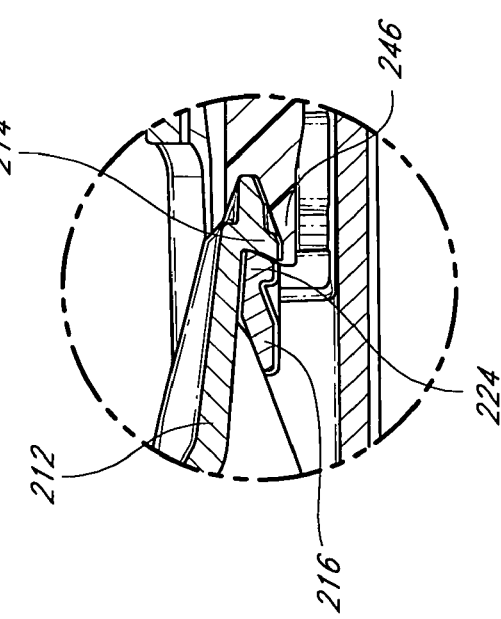
FIG. 11b
FIG. 11c

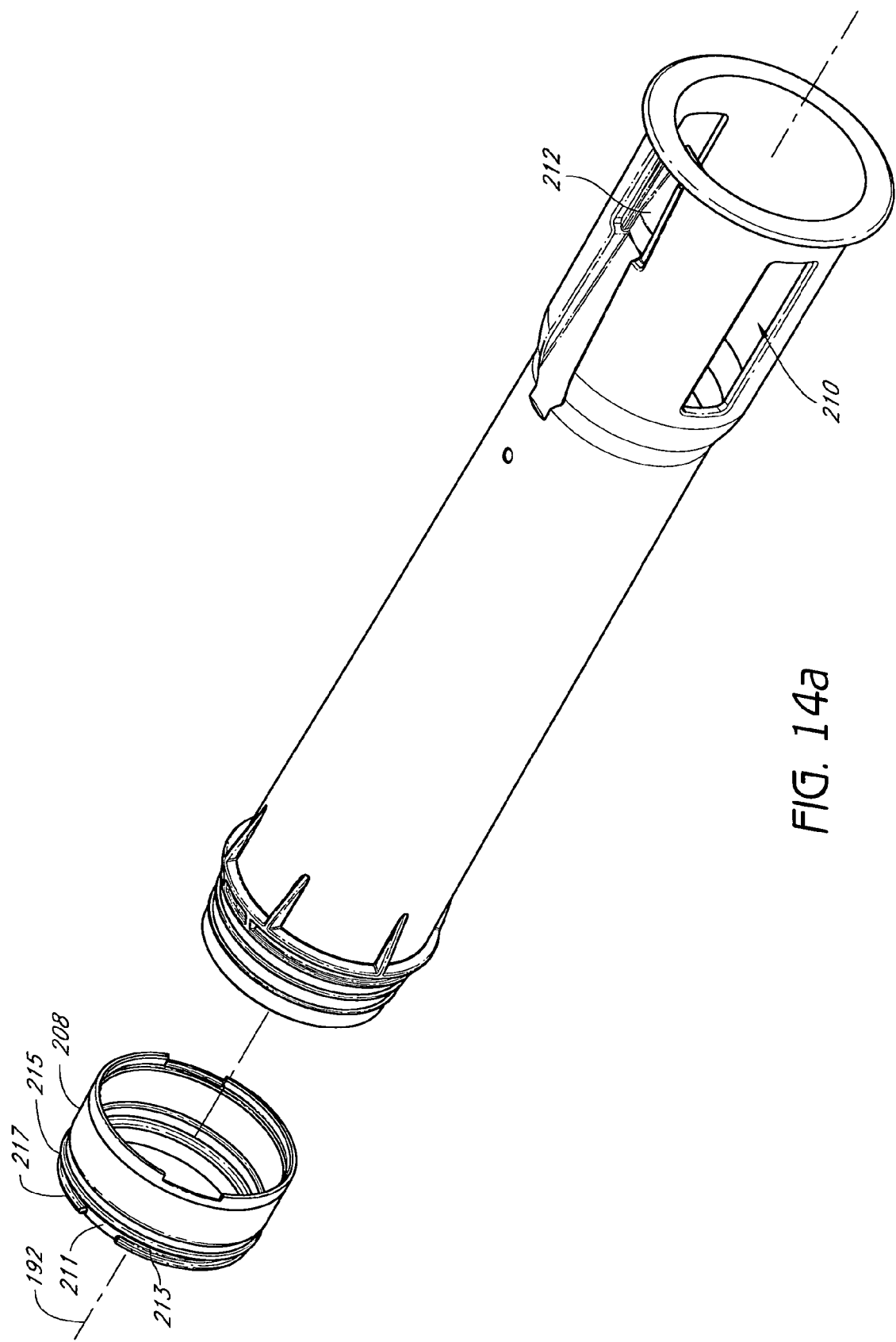

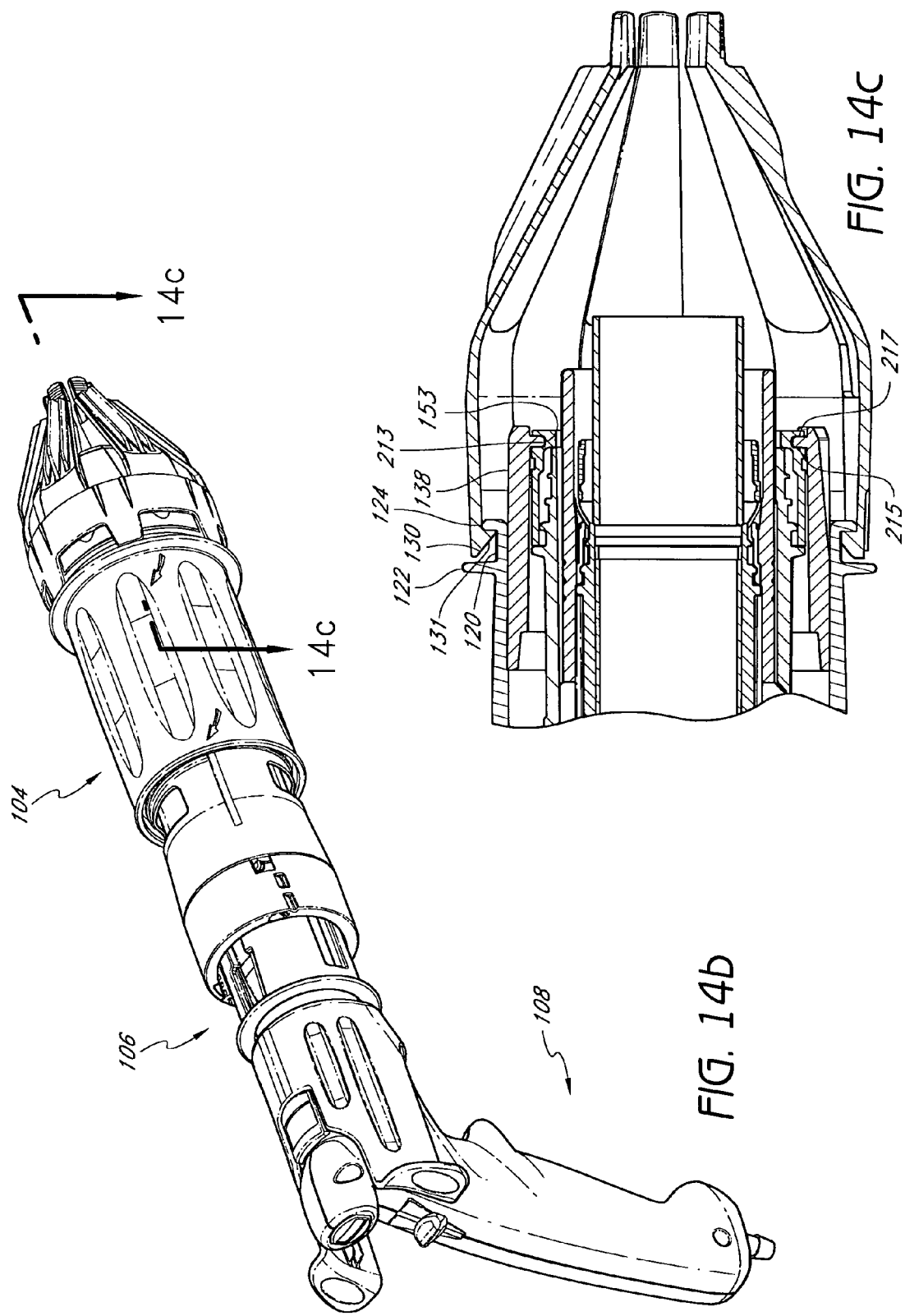

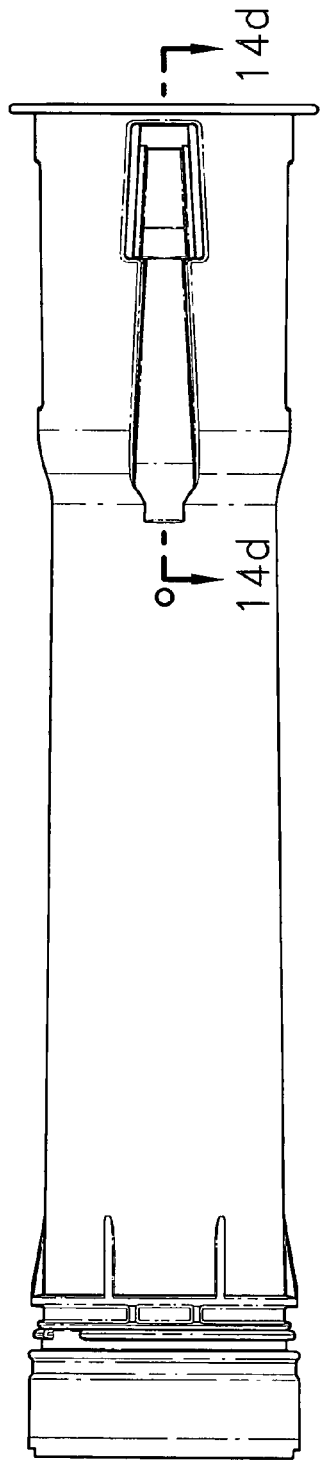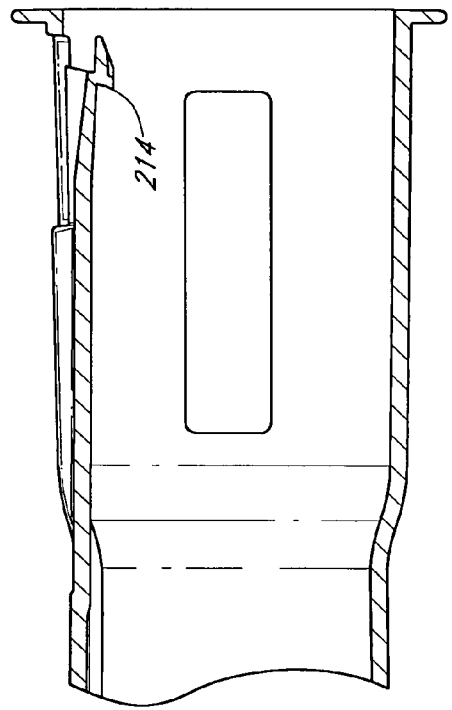
FIG. 14d
FIG. 14e

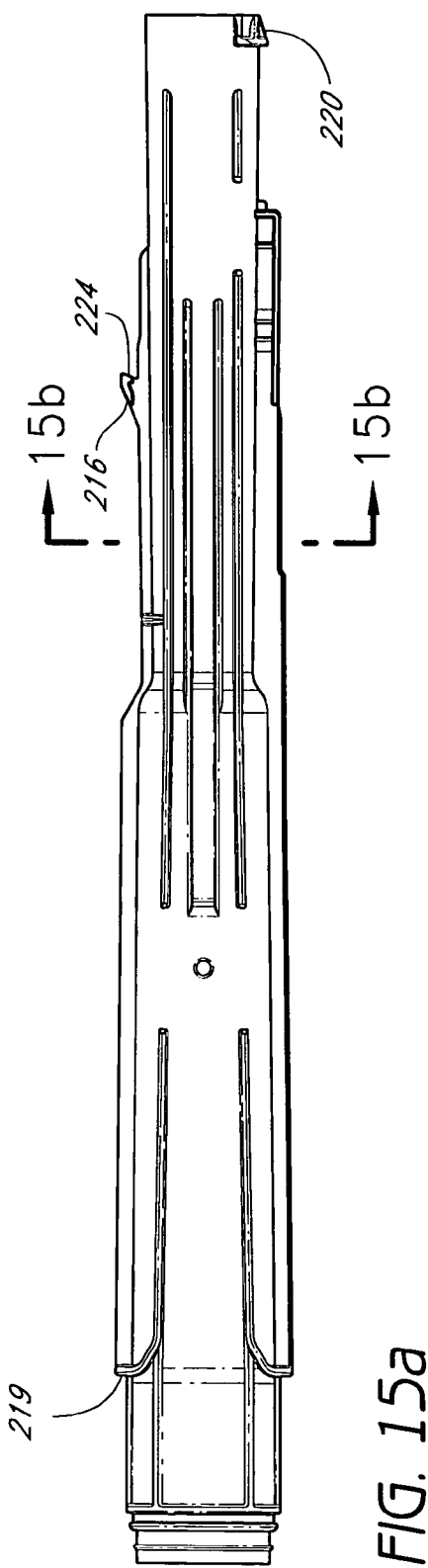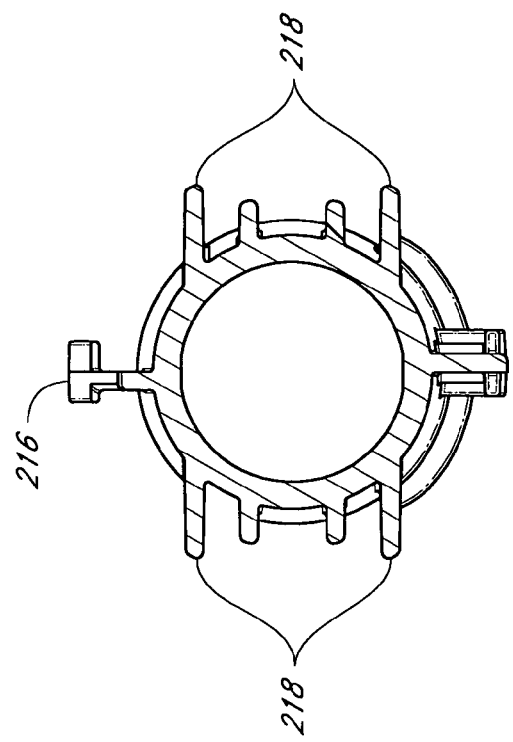
FIG. 15a
FIG. 15b

DEVICE TO DEPLOY A RESILIENT SLEEVE TO CONSTRICT ON BODY TISSUE

RELATED APPLICATION

This application claims the benefit of U.S. Provisional Patent Application Ser. No. 60/662,942, filed on Mar. 17, 2005, the entire contents of which are hereby incorporated herein by reference.

FIELD OF THE INVENTION

The preferred embodiment of this invention is generally directed to an apparatus for deploying a constriction device to portions of lung tissue for purposes of resection in order to treat Chronic Obstructive Pulmonary Disease (COPD).

BACKGROUND OF THE INVENTION

COPD has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991, COPD was the fourth leading cause of death in the United States and had increased 33% since 1979. COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Initially, hundreds of patients underwent a procedure called lung volume reduction surgery (LVRS), in which the most affected parts of the lungs are surgically removed. This procedure restores the tethering force that tends to keep intrathoracic airways open, which was lost in emphysema. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

Lung resection has a drawback in that it is difficult to seal against leaks once tissue has been resected. Lung tissue includes thin, fragile, and slippery blood vessels and air passageways that are difficult to suture against leaks. After the diseased tissue is removed, the remaining or resectioned lung portion is often restructured with suture staples. In about thirty percent of these cases, sutured lung tissue leaks air because the vessels were not adequately sealed. In other cases, sutured lung tissue leaks blood from the resection site for the same reason. Treatment for such leaks depends upon their severity, and often requires further open-chest surgery.

Previous efforts have been disclosed to treat COPD and other related pulmonary diseases by applying a constriction device to selected target tissue for purposes of resection in a manner that substantially minimizes the risk of leak, but also reduces the trauma resected with traditional lung volume reduction surgery. Such efforts are described in U.S. Pat. Nos. 6,328,689, 6,485,407, 6,491,706, 6,632,239, 6,589,161, 6,790,172 and 6,843,767, and U.S. application Ser. No. 09/901,764, all of which are incorporated herein by reference. In that regard, a constriction device having one of varying configurations can be selectively applied to a portion of target lung tissue by a delivery system, described somewhat schematically in one or more of the above patents. Such a delivery system has been disclosed in the prior art with more specific features that include an introducer and a loader in which the desired constriction is applied to a delivery system via a loader and then introduced onto the lung for release and ultimate resection. These prior art systems, while very beneficial in the delivery of such constriction devices, were more complicated to operate and required a multiple step operation that may be perceived adversely by the clinician. Thus, improvements have been made to a device capable of delivering a constriction device to a target lung portion, as described herein.

SUMMARY OF THE INVENTION

A preferred embodiment of the invention provides a method and apparatus to implant a tissue constriction device that improves therapy for COPD and suppresses leaks in organs and tissue without suturing.

One preferred embodiment provides an apparatus that deploys a resilient cylinder around body tissue. One purpose of the resilient cylinder is to constrict body tissue that may be diseased or leaking. Preferably, the function of the apparatus is to expand the resilient cylinder, retain the resilient cylinder in an expanded state, aspirate targeted body tissue within the confines of the expanded resilient cylinder, and release the resilient cylinder from the expanded state so that it constricts on to targeted body tissue.

One embodiment of the apparatus employs various components to perform these functions. A first component may be configured to expand the resilient cylinder by operation of an actuator and place resilient cylinder on to a second component. Preferably, the second component then cooperates with the first component to position the resilient cylinder on the second component and prepare the second component to deploy the resilient cylinder. Preferably, the first component and the second component are configured such that operation of the actuator causes: (i) the first component to expand the resilient sleeve and dispose it on the second component; and (ii) the first and second components to cooperate to prepare the apparatus to deploy the resilient sleeve. The preferred embodiment of the invention includes a vacuum source that aspirates the targeted body tissue into the confines of the expanded resilient sleeve. And, finally, the second component deploys the resilient sleeve so that it constricts on to the targeted body tissue.

One way in which the actuator is operated is through a "simple twist" feature. This "simple twist" feature simplifies and induces efficiency into what has been a complex, multi-step procedure. The "simple twist" improvement makes the device more user-friendly and facilitates training to operate the device. Further, because this novel feature reduces the chance of improper use of the device, the costs of medical procedures may be reduced.

Another embodiment of the invention is a method for resectioning lung tissue using a resilient sleeve. Preferably, the method comprises the steps of expanding the resilient cylinder, loading the resilient cylinder on a deployment device, and preparing the resilient cylinder on the deployment device such that the resilient cylinder is ready for releasable deployment. Preferably, one mechanical operation by the user is sufficient to expand, load and prepare the resilient cylinder for deployment.

A different embodiment is a device for deploying a resilient cylinder around a portion of body tissue that comprises a loading component and an introducing component. Preferably, the loading component is configured to expand the resilient cylinder and is moveable with respect to the loading component. The introducing component may comprise a first and second portion that are moveable with respect to each other in a first state and are not moveable with respect to each other in a second state. Preferably, the loading component and introducing component are configured such that movement of the loading component with respect to the introducing component expands the resilient cylinder and places the first and second components in the second state.

BRIEF DESCRIPTION OF THE DRAWINGS

FIG. 1b is a perspective view of one embodiment of a resilient sleeve.

FIG. 1c is a cross-sectional view of the resilient sleeve of FIG. 1b.

FIG. 4a is a side view of the retractor of FIG. 4.

FIG. 4b is an end view of the retractor of FIG. 4.

FIG. 7 is a perspective view of one embodiment of a finger tab guide.

FIG. 7a is a cross-sectional view of a single protrusion located on the finger tab guide of FIG. 7.

FIG. 8 is a side view of one embodiment of an operating cylinder.

FIG. 8a is a detail view of the securing recesses located on the operating cylinder of FIG. 8.

FIG. 11b is a cross-sectional assembled view of an embodiment of the device of FIG. 11.

FIG. 11c is an enlarged view of a portion of the device depicted in FIG. 11b.

FIG. 14a is an exploded view of the actuating cylinder of FIG. 14.

FIG. 14b is a perspective view of the assembled device with the actuating cylinder of FIG. 14.

FIG. 14c is a cross-sectional view of a portion of the assembled device with the actuating cylinder of FIG. 14.

FIG. 14d is a top view of a portion of the actuating cylinder of FIG. 14.

FIG. 14e is a cross-sectional view of the actuating cylinder of FIG. 14.

FIG. 15a is a side view of the locking cylinder of FIG. 15.

FIG. 15b is a cross-sectional view of the locking cylinder of FIG. 15

DETAILED DESCRIPTION OF THE PREFERRED EMBODIMENT

The preferred embodiment contemplates a device configured to prepare and deploy a resilient sleeve 100 on to a portion of body tissue. This device expands the resilient sleeve 100, uses a vacuum system to draw the body tissue into resilient sleeve 100, and releases resilient sleeve 100 from the expanded state so that it captures and constricts the body tissue.

A preferred embodiment of resilient sleeve 100 is depicted in FIGS. 1b and 1c. In alternative embodiments, the device may prepare and deploy a resilient part of different shape, such as a cylindrical ring similar to a ligation band. For example, some embodiments of resilient sleeves that may be used are described in the patents and applications described above.

Figure 1:
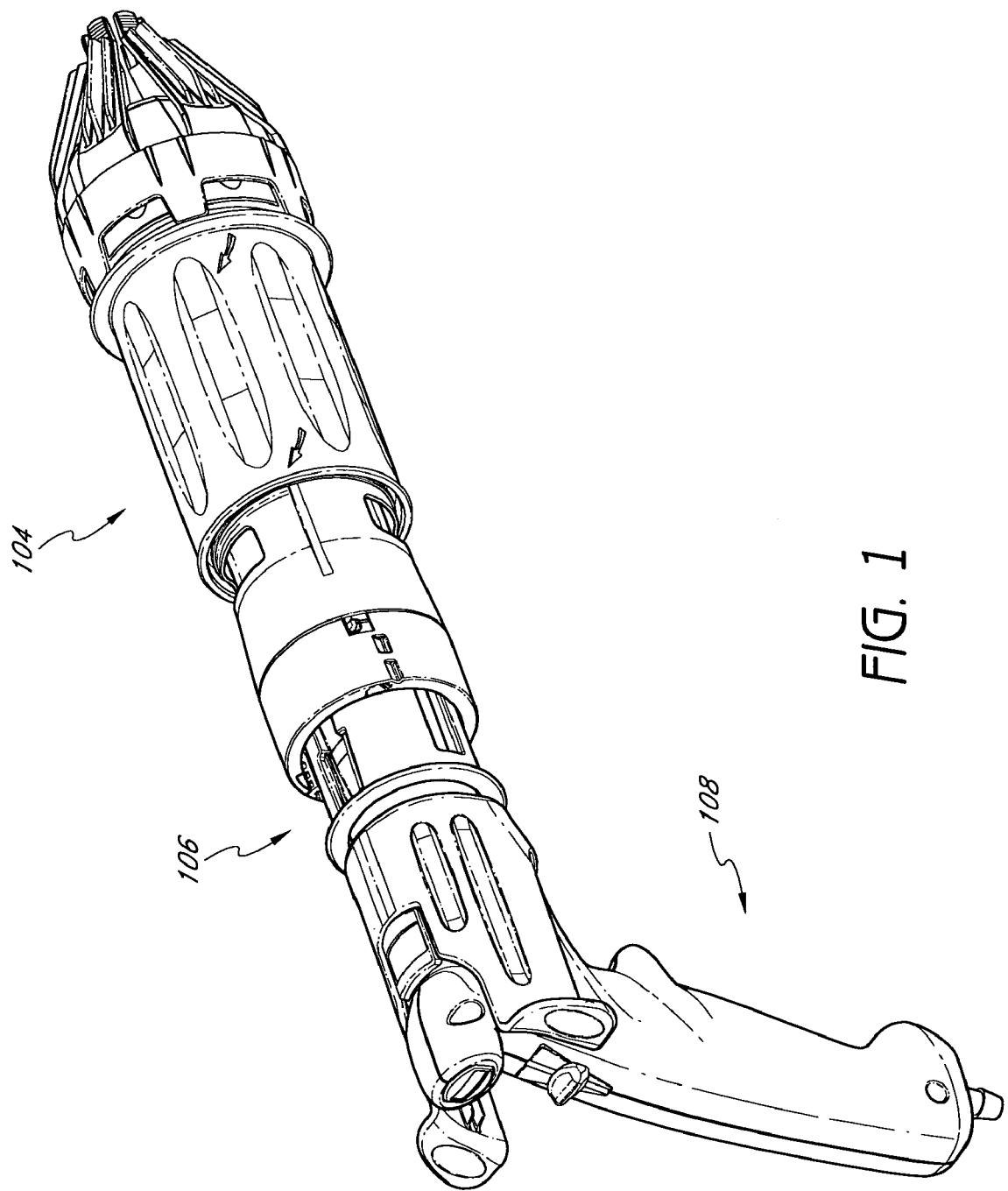
FIG. 1 illustrates a perspective view of one embodiment of a fully assembled device in accordance with the principles disclosed herein.

The preferred embodiment of the invention employs a loading component 104 to expand and load resilient sleeve 100 on to an introducing component 106. Preferably, introducing component 106 then cooperates with the loading component 106 to position resilient sleeve 100 on introducing component 106 and prepare introducing component 106 to deploy resilient sleeve 100. Preferably, a vacuum system connected to a handle component 108 is used to draw the body tissue into resilient sleeve 100. Introducing component 106 is also preferably configured to deploy the resilient sleeve 100 on to the body tissue. FIG. 1 depicts the invention fully assembled. One aspect of a preferred embodiment is that a "simple twist" operation expands resilient sleeve 100, loads resilient sleeve 100 on to introducing component 106, and prepares the device to deploy resilient sleeve 100.

Loading Component

Figure 2:
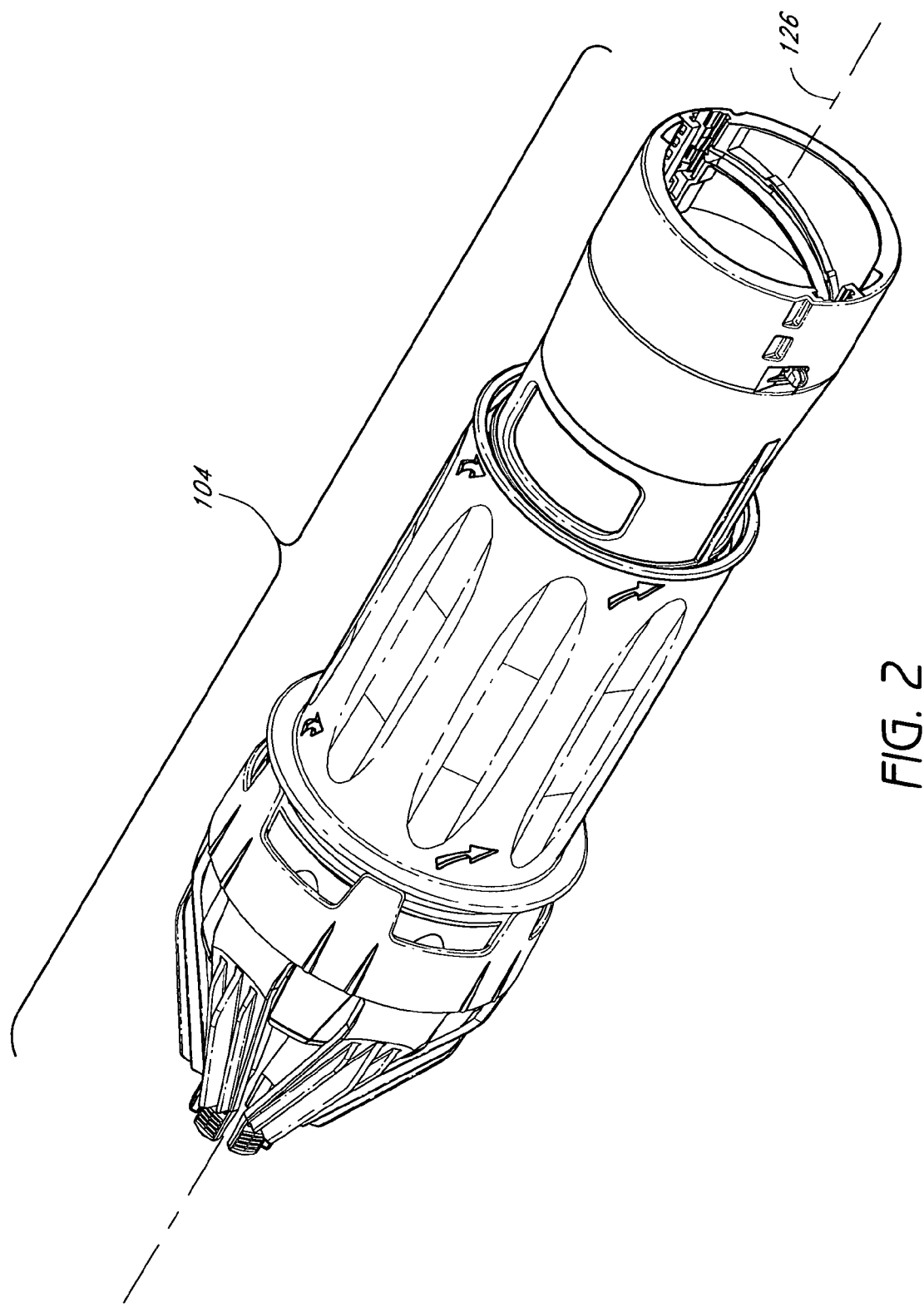
FIG. 2 is an assembled view of one embodiment of a loading component.
Figure 2A:
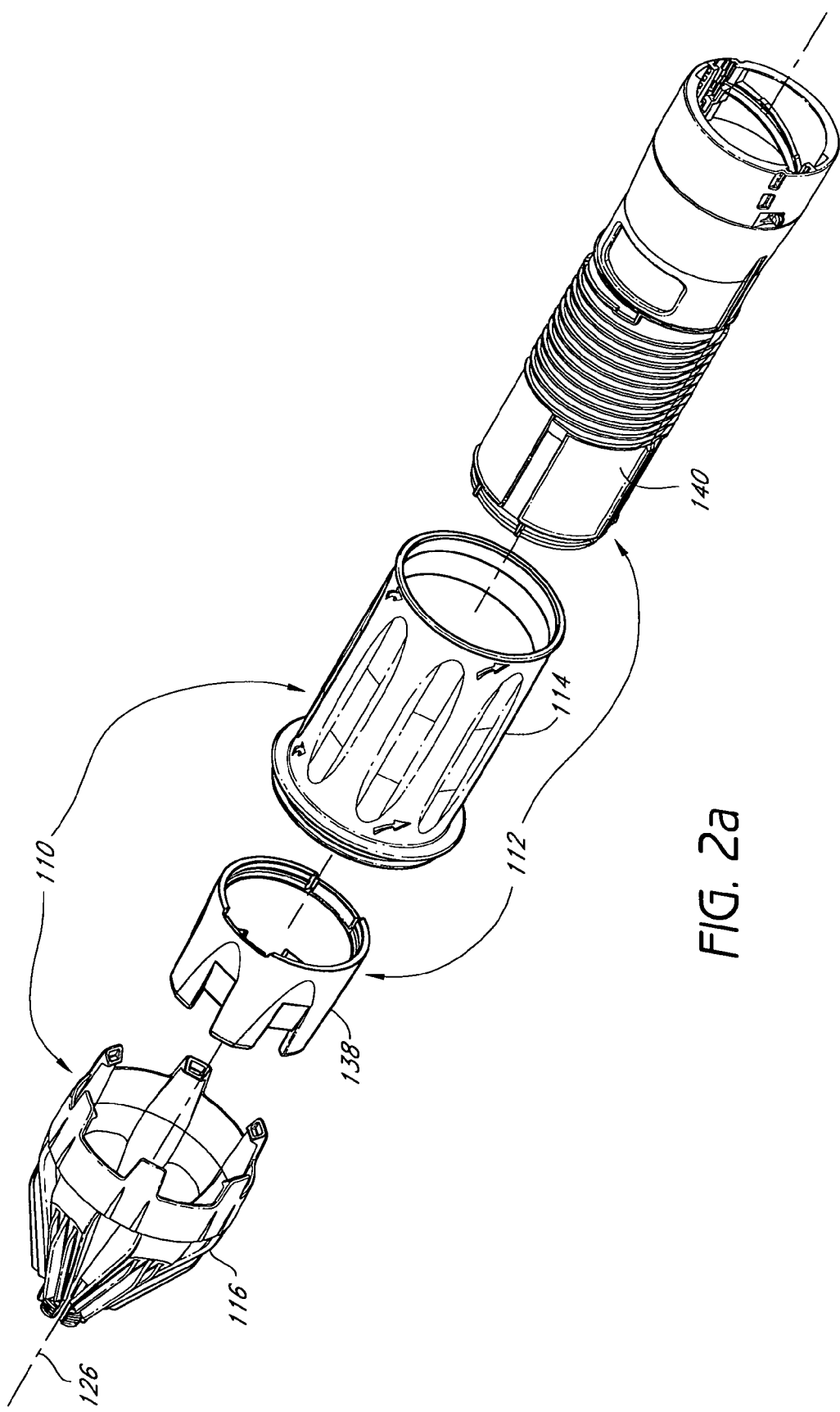
FIG. 2a is an exploded view of the loading component of FIG. 2.

The loading component 104 preferably expands resilient sleeve 100 and places resilient sleeve 100 on to introducing component 106. The assembled loading component is depicted in FIG. 2. Preferably, loading component 104 is comprised of a retracting cylinder 110 and guide cylinder 112, as shown in FIG. 2a. Axis 126 is the axis common to the retracting cylinder 110 and guide cylinder 112. In alternative embodiments, loading component 104 may be comprised of a single part or be of non-cylindrical shape. Further, the loading component may be of any suitable design that adequately expands and places the resilient sleeve 100 on to introducing component 106. Advantageously, a cylindrically shaped loading component 104 is consistent with the shape of resilient sleeve 100 and facilitates relative movement with a cylindrically shaped introducing component 106. The cylindrical shape also allows relative rotational movement between various parts of the device, and, advantageously, rotational relationships are a consistent and accurate means to guide relative movement.

Retracting Cylinder

Figure 3:
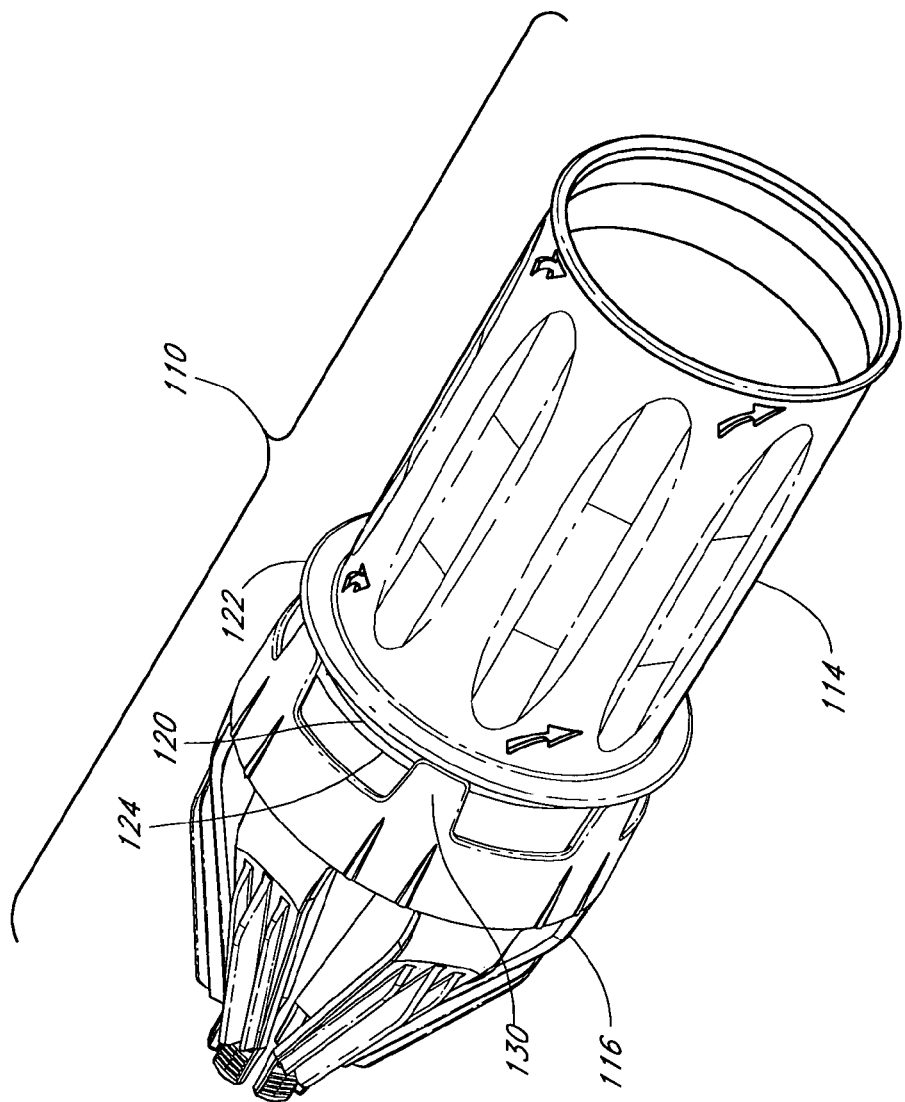
FIG. 3 is an assembled view of one embodiment of a retracting cylinder.
Figure 4:
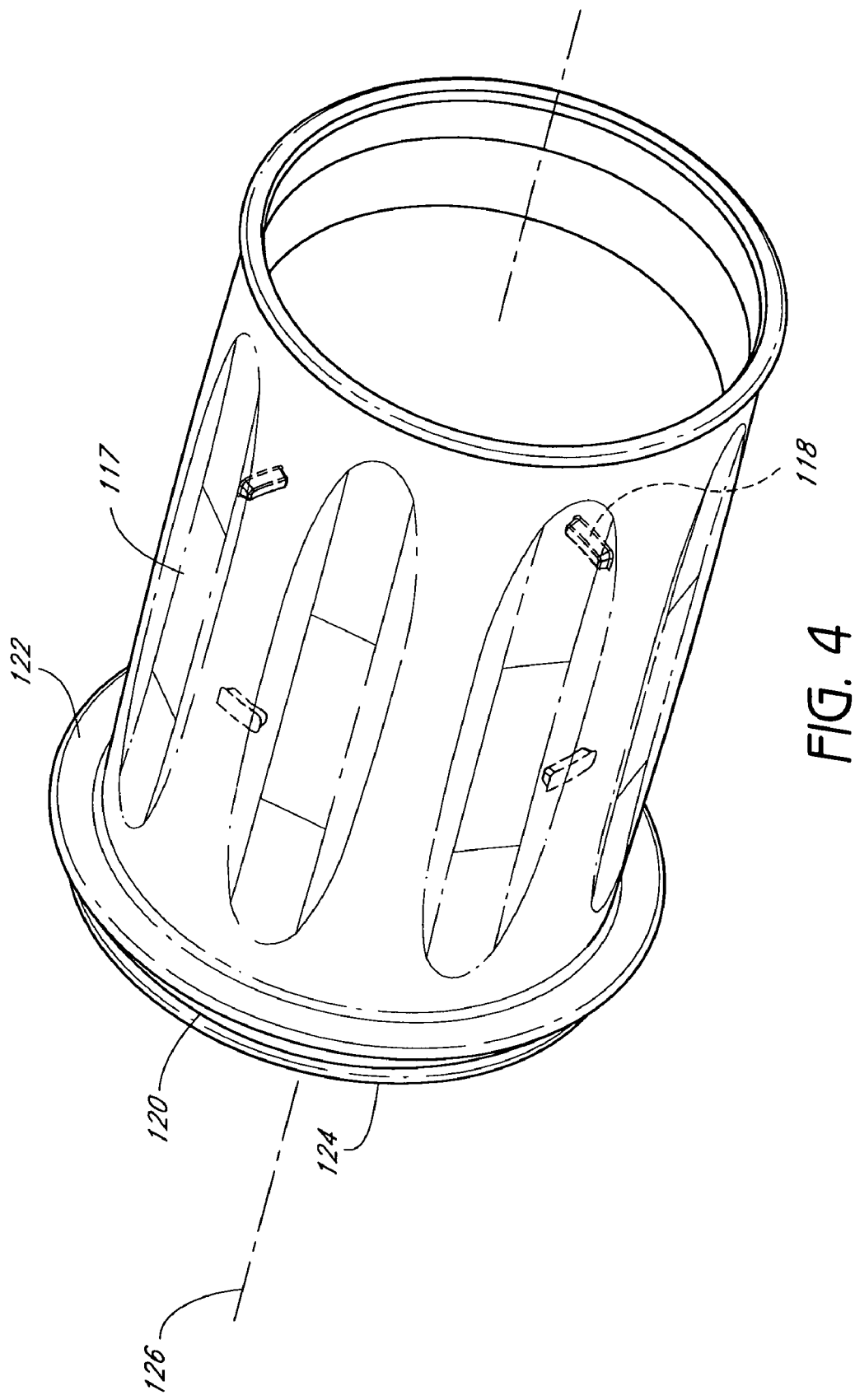
FIG. 4 is a perspective view of one embodiment of a retractor.

The retracting cylinder 110, depicted in FIG. 3, may be comprised of a retractor 114 and an expander 116. As shown in FIG. 4, retractor 114 may have gripping grooves 117 on its external surface, thread tabs 118 on its internal surface, and an expander groove 120 at its distal end. However, other embodiments of the retractor may have any type of gripping surface that facilitates operation of the retractor or no gripping surface at all. Advantageously, gripping grooves 117 provide an ergonomic and secure surface for operators to grasp and twist retractor 114. Desirably, retractor 114 is constructed by shaping an extruded or molded plastic-type material such as acetal copolymer. In alternative embodiments other material types and manufacturing methods may be utilized that are appropriate for constructing components for this type of medical device.

In the preferred embodiment, there are four raised thread tabs 118 equally spaced radially at a mid-portion along the length of retractor 114. Preferably, thread tabs 118 are shaped and oriented such that they cooperate to function as a helical thread. See FIGS. 4a and 4b. In alternative embodiments, there may be any number of thread tabs or the thread tabs may cooperate to function as more than one helical thread. In further embodiments, the relative motion (described below) between retracting cylinder 110 and guide cylinder 112 may be guided in a different manner, eliminating the need for any thread tabs at all. For example, the relative movement between the retracting cylinder 110 and guide cylinder 112 may be only in the axial direction and may be guided by grooves and guides as opposed to threads, or it may be completely unguided. Advantageously, a rotational relationship guided by threads provides a steady and precise means to retract retracting cylinder 110 and expand resilient sleeve 100.

In the preferred embodiment, expander groove 120 operates to link retractor 114 to expander 116. Preferably, expander groove 120 is shaped by two circularly shaped walls (122, 124) extending outward from and normal to the external surface of retractor 114. Wall 122 may be located a short distance along axis 126 from wall 124 such that a plurality of retractor tabs 130 (described below) reside between the walls (122, 124), as shown in FIG. 4.

Figure 5:
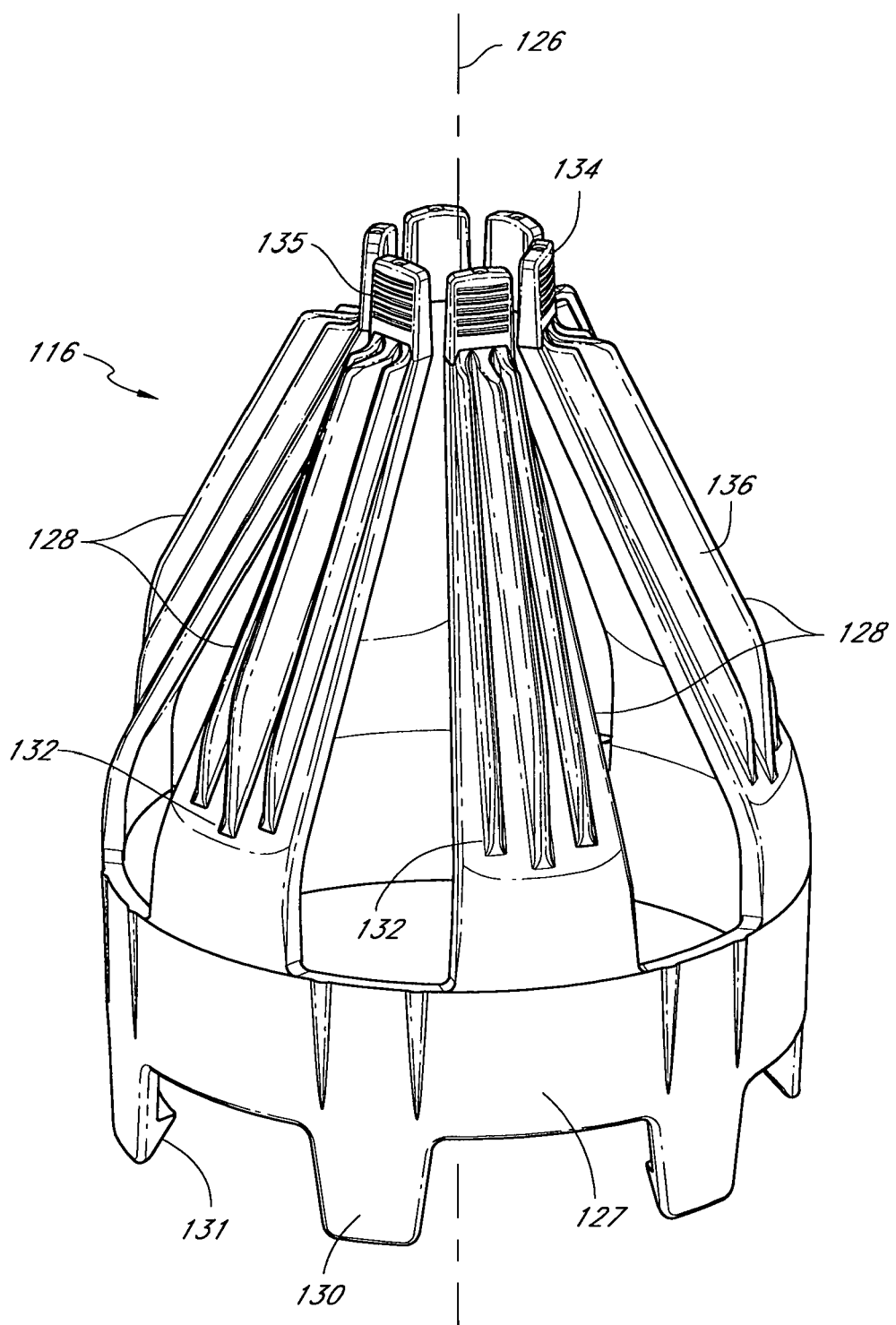
FIG. 5 is a perspective view of one embodiment of an expander.

In the preferred embodiment, expander 116, depicted in FIG. 5, has a cylindrical body 127 with a proximal and distal end, finger tabs 128 extending distally from the distal end of cylindrical body 127, and retractor tabs 130 extending proximally from the proximal end of cylindrical body 127. Preferably, each finger tab 128 is comprised of a finger body 132 and a finger tip 134. However, in other embodiments, the finger tabs may be of any other suitable configuration or shape that adequately grips and expands resilient sleeve 100. Desirably, expander 116 may be constructed by shaping a molded plastic-type material such as polycarbonate. In alternative embodiments other material types and manufacturing methods may be utilized that are appropriate for constructing components for this type of medical device.

In the preferred embodiment, each retractor tab 130 has a proximal end from which a retractor catch 131 extends normal to axis 126. See FIG. 5. Retractor catches 131 may reside within expander groove 120 to rotatably couple and limit relative axial movement between retractor 114 and expander 116. However, this is not a required feature of the invention and alternative embodiments may limit relative rotation between retractor 114 and expander 116. In other embodiments, retractor 114 and expander 116 may be linked in any other suitable manner.

Finger bodies 132 are preferably equally spaced from each other radially and extend distally from the distal end of the cylinder body 127. Distal from cylinder body 127, finger bodies 132 angle toward axis 126 without crossing axis 126. See FIG. 5. Preferably, the width of each finger body 132 gradually decreases from its proximal to distal end. In alternative embodiments, the finger bodies may be hinged to each other and extend up to or beyond axis 126 such that resilient sleeve 100 is expanded by the interdependent movement of the finger bodies with respect to each. Further, it is contemplated that the finger bodies may be of constant width. Advantageously, finger bodies 132 in the preferred embodiment provide a simple design in which each finger body acts similarly yet independent of each other in expanding resilient sleeve 100. Additionally, because finger bodies 132 angle towards axis 126, they form a smaller diameter at their distal end, and the decreasing width of each finger body 132 allows the distal end of the finger bodies as a whole to fit within this smaller diameter.

Preferably, finger bodies 132 are strengthened by support ribs 136 fixed along the length of finger bodies 132. There may be three support ribs 136 that extend longitudinally on the outside surface of each finger body 132, as shown in FIG. 5. In other embodiments, there may be any number of support ribs, the support ribs may be placed in any suitable location, any other suitable means may be used to reinforce the finger bodies 132, or the finger bodies may not be reinforced at all.

Advantageously, longitudinal support ribs 136 allow finger bodies 132 to withstand the stress caused by expansive or contractive forces at their distal end.

In the preferred embodiment, each finger tip 134 is fixedly attached to the distal end of a respective finger body 132 and extends distally and slightly away from axis 126. See FIG. 5. Preferably, finger tips 134 have raised lateral bumps 135 along the width of their outside surface to provide a gripping surface for resilient sleeve 100. Preferably, the length of finger tips 134 is sufficient to allow them to securely grip resilient sleeve 100 when resilient sleeve 100 is expanded. In some embodiments, finger tips 134 may extend in any direction relative to axis 126. Further, the gripping surface of finger tips 134 may be designed in any other suitable manner or it may not be present at all. Advantageously, finger tips 134 that are angled slightly away from axis 126 and that have lateral bumps 135 prevent resilient sleeve 100 from slipping off the distal end of expander 116. In other embodiments, the retractor cylinder may be constructed of one or any number of parts. Advantageously, retractor 114 and expander 116 are rotatably coupled and provide stability during the loading process because expander 116, finger tabs 128 and resilient sleeve 100 are insulated from the rotation of retractor 114.

In alternative embodiments, the loader component may be of any other design suitable to place resilient sleeve 100 on to introducing component 106 in an expanded state. Loader component 104 may be constructed of any number of parts and may not comprise a separate retractor 114 and expander 116. In other embodiments, the loading component may not employ finger tabs 128 and may use any suitable surface capable of expanding to a diameter greater than the non-expanded diameter of resilient sleeve 100.

Guide Cylinder

Figure 6:
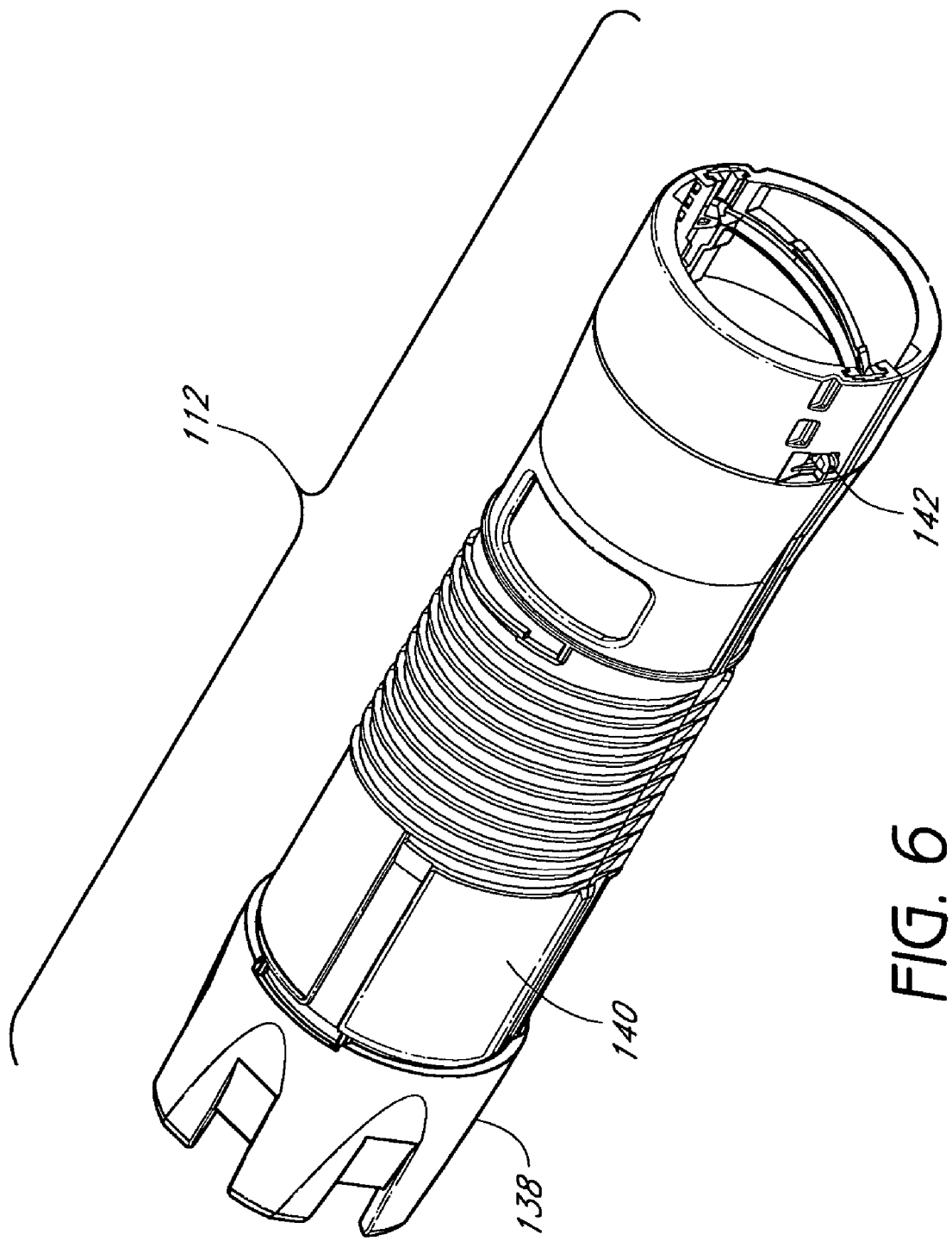
FIG. 6 is an assembled view of one embodiment of a guide cylinder

In the preferred embodiment, guide cylinder 112 cooperates with retracting cylinder 110 to expand and load resilient sleeve 100. Preferably, guide cylinder 112, depicted in FIGS. 6 AND 6a, includes a finger tab guide 138, an operating cylinder 140, and loader locks 142.

In the preferred embodiment, finger tab guide 138 is cylindrical in shape and snap-fit to the distal end of guide cylinder 112. Desirably, finger tab guide 138 is constructed by shaping and/or cutting an extruded or molded plastic-type material such as acetal copolymer. In alternative embodiments other material types and manufacturing methods may be utilized that are appropriate for constructing components of this type of medical device. Preferably, finger tab guide 138 is comprised of a cylindrical portion with six rectangular shaped protrusions 152 extending distally therefrom and compression tabs 153 near the distal end of protrusions 152, as shown in FIG. 7. Preferably, protrusions 152 are equally spaced radially with respect to axis 126, providing rectangular shaped gaps between each protrusion 152. See FIG. 7. The cross section 154 of each protrusion that is parallel to the plane normal to axis 126 increases in thickness from one edge 156 of each protrusion to the other edge 158. See FIG. 7a. Preferably, protrusions 152 have a minimum thickness ($T_1$) at one edge 156 of cross section 154 and gradually increase to a maximum thickness ($T_2$) at a point less than half way across the width of each protrusion 152, and the thickness remains constant from this point to the opposite edge 158 of each protrusion 152. The edge 158 having a maximum protrusion thickness may be angled in the towards edge 156 of the same protrusion 152, as indicated in FIG. 7a. Alternative embodiments may provide for different shaped cross sections of the protrusions. In other embodiments the finger guide may not include any protrusions and be of continuous cylindrical or any other suitable shape. Advantageously, the rectangular gaps between protrusions 152 and the design of protrusions 152 guide, align and secure finger tabs 128 during the expansion process.

Preferably, two compression tabs 153 extend from the internal surface of and near the distal end of finger tab guide 138 normal to protrusions 152 and toward axis 126. See FIG. 7. Preferably, compression tabs 153 are diametrically opposed to each other and located near the center of opposing protrusions 152. In other embodiments there may be any number of compression tabs.

In the preferred embodiment of the invention, operating cylinder 140 may be constructed in two halves to facilitate manufacturing. Operating cylinder 140 may be constructed by shaping an extruded or molded plastic-type material such as acetal copolymer. In alternative embodiments other material types and manufacturing methods may be utilized that are appropriate for constructing components of this type of medical device. Desirably, operating cylinder 140 includes external threads 144, securing recesses 146, locking grooves 148, release channels 150, and loader lock housings 151, as shown in FIG. 8. In the preferred embodiment, thread tabs 118 of retractor 114 reside within threads 144. Thread tabs 118 and threads 144 cooperate to guide relative movement between retracting cylinder 110 and guide cylinder 112. Threads 144 may be of helical shape and extend along an intermediate portion of the length of guide cylinder 112. In other embodiments, threads 144 or thread tabs 118 may be absent, and relative motion between retracting cylinder 110 and guide cylinder 112 may be guided in any suitable manner. Advantageously, a rotational relationship guided by threads provides a steady and precise relative movement between retracting cylinder 110 and guide cylinder 112.

In this embodiment of the invention, two securing recesses 146 are located at a proximal end of threads 144 on the external surface of operating cylinder 140. See FIG. 8. Each securing recess 146 may include four raised walls (160, 161, 162, 163), as depicted in FIG. 8a. Wall 160 may be substantially parallel to axis 126 and extend distally from the proximal end-points of threads 144. Wall 161 may extend substantially parallel to threads 144 from the distal most point of wall 160. Wall 162 may be substantially parallel to axis 126 and extend proximally from the proximal end of wall 161 until it meets wall 163. Wall 163 may be a circular lip extending radially away from axis 126, and may be located at a distance from the proximal most point of wall 160 that is greater than the thickness of thread tabs 118. In alternative embodiments movement between retracting cylinder 110 and guide cylinder 112 may be restricted by other suitable means. For example, movement may be restricted by employing a lock tab on the retracting cylinder that engages a releasable lock catch on the operating cylinder. Advantageously, securing recesses 146 as described simplify the manufacturing and operation of loading component 104 by utilizing features necessary for other functions. For example, the preferred design allows thread tabs 118 to restrict rotation after guiding the relative rotation between the retracting and guide cylinders (110, 112). Advantageously, securing recesses 146 in the preferred embodiment are created as an extension of threads 144, which facilitates manufacturing.

In the preferred embodiment, two helical locking grooves 148 are provided Preferably, locking grooves 148 are located on the internal surface of operating cylinder 140 and extend distally from a proximal point on the operating cylinder 140 to an intermediate point along the length of operating cylinder 140. Preferably, locking grooves 148 are raised from the internal surface of operating cylinder 140 and extend radially toward axis 126. In alternative embodiments other mechanisms may be used to move loading component 104 proximally relative to introducing component 106. Advantageously, locking grooves 148 allow the continued use of relative rotation (here, the rotation is between loading component 104 and introducing component 106) to further prepare resilient sleeve 100 for deployment.

Figure 8B:
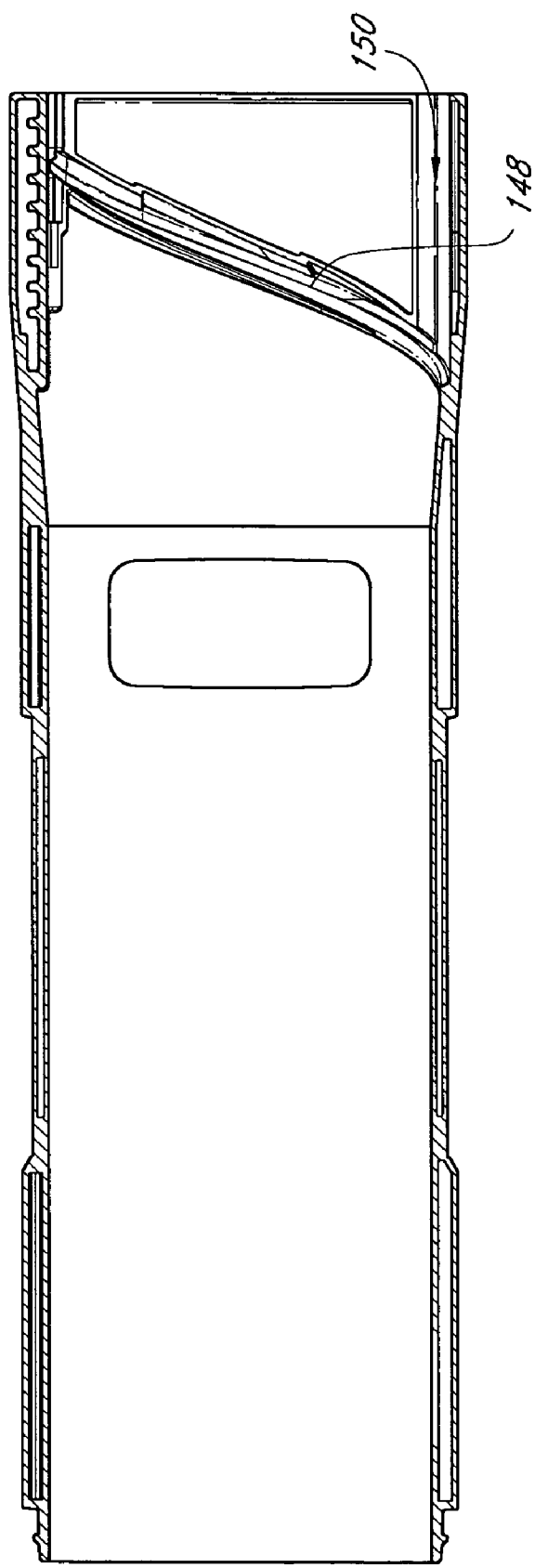
FIG. 8b is a cross-sectional view of the operating cylinder of FIG. 8.

The preferred embodiment includes release channels 150 located on an internal surface of operating cylinder 140 that extend between the distal end of locking grooves 148 and the proximal end of operating cylinder 140, as illustrated in FIG. 8b. The preferred embodiment also includes Channel tabs 188 located on retainer 174 of introducing component 106. Channel tabs 188 are described in more detail below. Preferably, the width of release channels 150 slightly greater than the width of channel tabs 188.

Figure 6A:
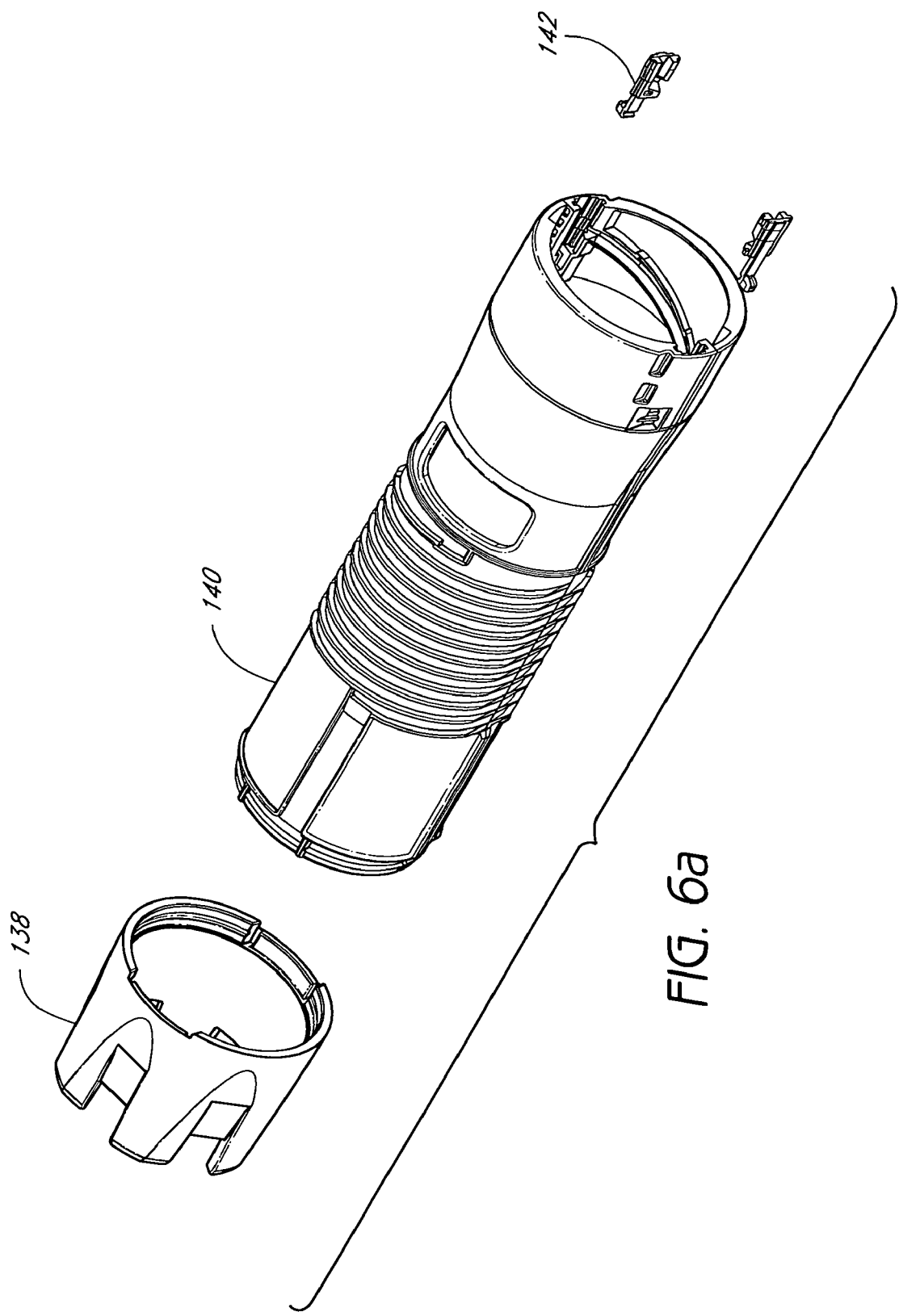
FIG. 6a is an exploded view of the guide cylinder of FIG. 6.
Figure 9A:
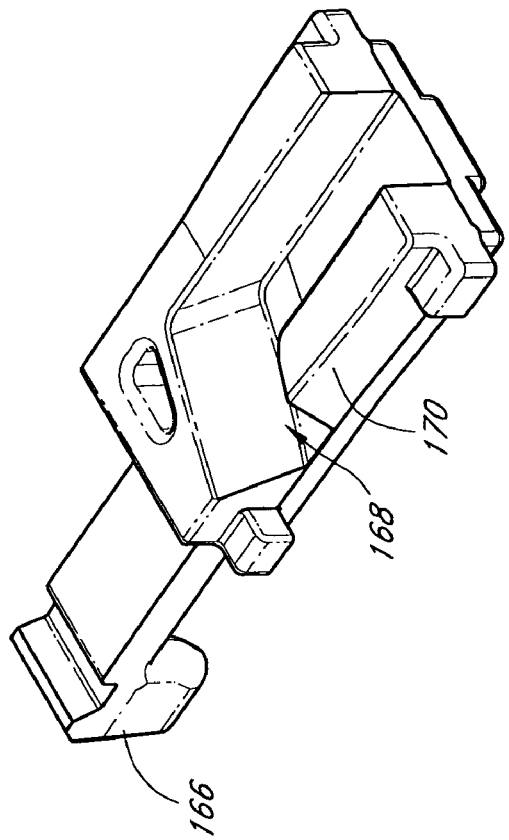
FIG. 9a is a perspective view of the other side of the loader locks of FIG. 9.
Figure 9:
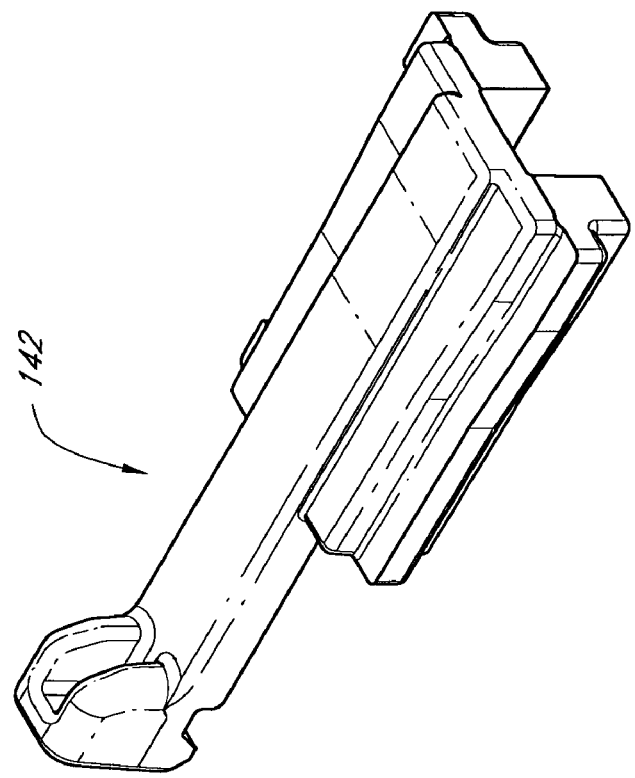
FIG. 9 is a perspective view of one embodiment of the loader locks.

As illustrated in FIG. 6A, the preferred embodiment provides two loader locks 142 located diametric to each other at the proximal end of operating cylinder 140. Preferably, loader locks 142 cooperate with channel tabs 188 to limit rotation and axial movement between loading component 104 and introducing component 106. See FIG. 2. Preferably, each loader lock 142 is comprised of a loader lock button 166, loader lock groove 168, and loader lock catch 170. See FIGS. 9 and 9a. Preferably, the loader lock catch 170 prevents channel tabs 188 (described below) from entering locking grooves 148 (described below) when loader lock 142 is in the locked position. In this embodiment, the loader lock 142 is unlocked when loader lock button is moved proximally. Each loader lock groove 168 may be oriented so that it is aligned with and follows the helical profile of a respective locking groove 148 (described below) when loader lock 142 is in the unlocked position.

As shown in FIG. 2, guide cylinder 112 is preferably located concentric and internal to the retracting cylinder 110. Prior to rotating retractor 114, the inner diameter of the portion of expander 116 that is distal to the point of contact between the expander 116 and the finger tab guide 138 is less than the diameter of finger tab guide 138. Further, because finger tabs 128 are angled toward axis 126, the inner diameter of expander 116 decreases gradually approaching the distal end of retracting cylinder 110.

Expansion Process

Figure 10:
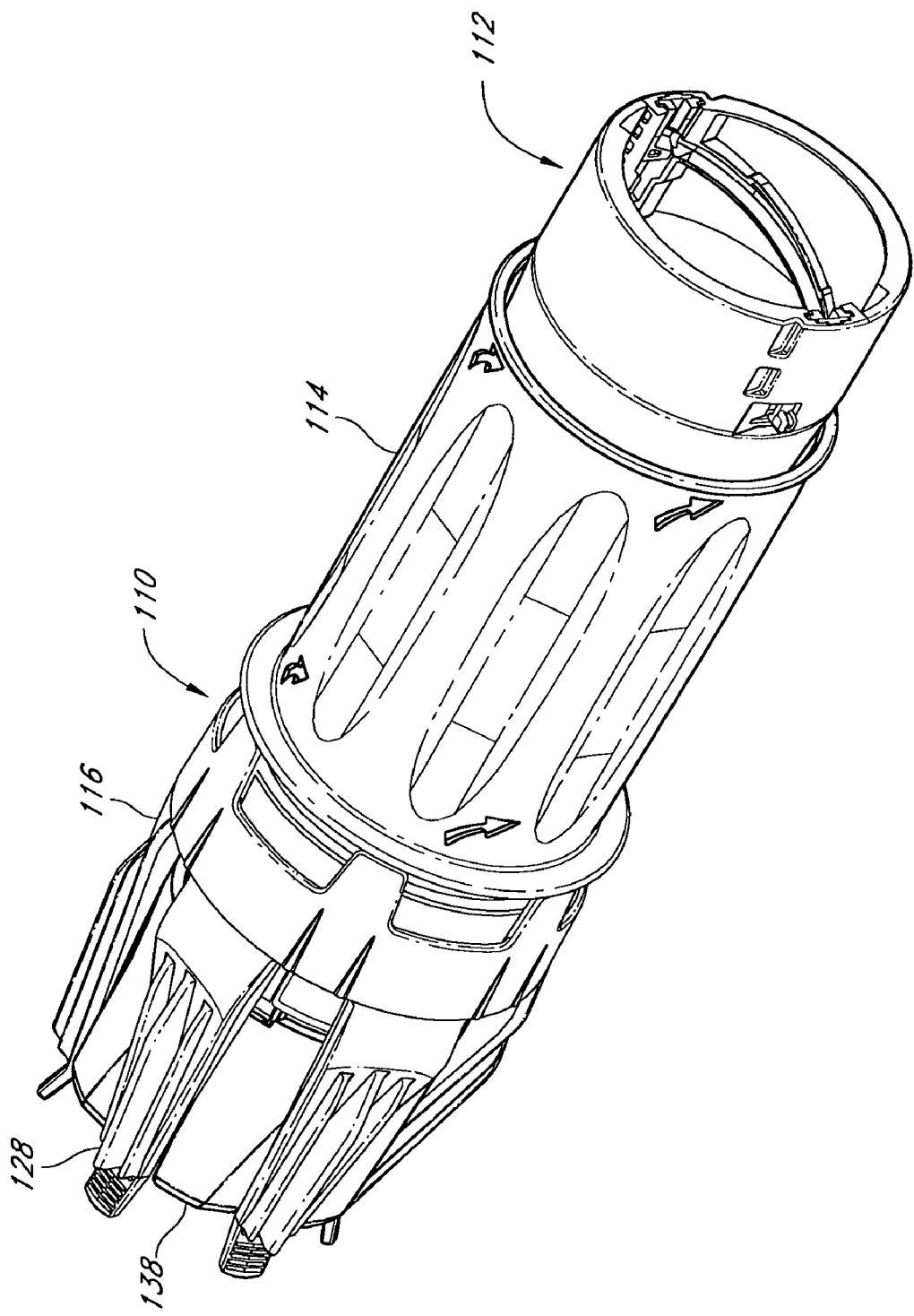
FIG. 10 is a perspective view of the loading component of FIG. 2 with the retracting cylinder moved proximally relative to the guide cylinder.

Upon rotation of retractor 114 in the preferred embodiment, threads 144 cooperate with the thread tabs 118 to move retracting cylinder 110 proximally relative to guide cylinder 112. As retracting cylinder 110 moves proximally relative to finger tab guide 138, a more distal point of the angled finger tabs 128 (corresponding to a smaller expander 116 inner diameter) contacts the finger tab guide 138. This causes finger tabs 128 to gradually spread to match the fixed diameter of finger tab guide 138 as retracting cylinder 110 is drawn proximally relative to guide cylinder 112. FIG. 10 shows retracting cylinder 110 displaced proximally relative to guide cylinder 112 and the corresponding expansion of finger tabs 128.

In the preferred embodiment, as retractor 114 draws expander 116 proximally, finger tabs 128 are contained between protrusions 152 of finger tab guide 138. See FIG. 10. This limits relative rotation between expander 116 and guide cylinder 112. One side of each finger tab 128 is constrained by the angled edge 158 of each protrusion 152, thereby limiting relative rotation between expander 116 and the guide cylinder 112 in the counter-clockwise direction. The other side of each finger tab 128 may contact a different protrusion 152 at a point where protrusion 152 is increasing in thickness. Clockwise rotation between expander 116 and guide cylinder 112 is therefore limited because finger tabs 128 are faced with the "uphill" prospect of traversing the outer surface of protrusions 152 from a smaller to a greater thickness. Alternative embodiments may allow rotation between expander 116 and guide cylinder 112. Advantageously, limiting rotation between guide cylinder 112 and expander 116 (and therefore the resilient sleeve 100) provides stability during the expansion process and prevents resilient sleeve 100 from twisting or loading unevenly.

After traveling the length of threads 144, thread tabs 118 in the preferred embodiment enter securing recesses 146 through the distance ($D_1$) between wall 162 and 163. See FIG. 8. Because the finger tabs are angled toward axis 126, the expansion of expander 116 against finger guide 138 biases retracting cylinder 110 distally. The effect of this bias is to pull thread tabs 118 distally to contact wall 161 after thread tabs 118 enter securing recesses 146. Thread tabs 118 are now captured by the four walls (160, 161, 162, 163) of securing recesses 146 thereby limiting relative movement between retracting and guide cylinders (110, 112) in four directions (proximal, distal, clockwise and counter-clockwise). As discussed above, other suitable means may be employed to limit motion between retracting cylinder 110 and guide cylinder 112, but the use of securing recesses 146 simplifies the manufacture and operation of loading component 104.

As retractor 114 is drawn proximally in this embodiment, the proximal end of retractor 114 contacts and compresses loader locks 142 thereby moving loader lock catches 170 proximally and releasing channel tabs 188. Releasing loader lock tabs 189 in this embodiment allows relative movement between loading component 104 and introducing component 106. It is contemplated that relative movement between these two components may be restricted and released in other suitable manners. Advantageously, the preferred embodiment allows the loader locks 142 to be unlocked through the continued rotation of retractor 114, which simplifies and facilitates the expansion process.

Further, the entire expansion process is accomplished by rotation of retractor 114. This "simple twist" feature makes the device very simple to operate and reduces the possibility of operator error. The simple and efficient design should increase the efficiency of medical procedures that utilize the invention. Additionally, because improper use is less likely, the "simple twist" feature may reduce costs resulting from damaged or wasted devices.

Introducing Component

Figure 11:
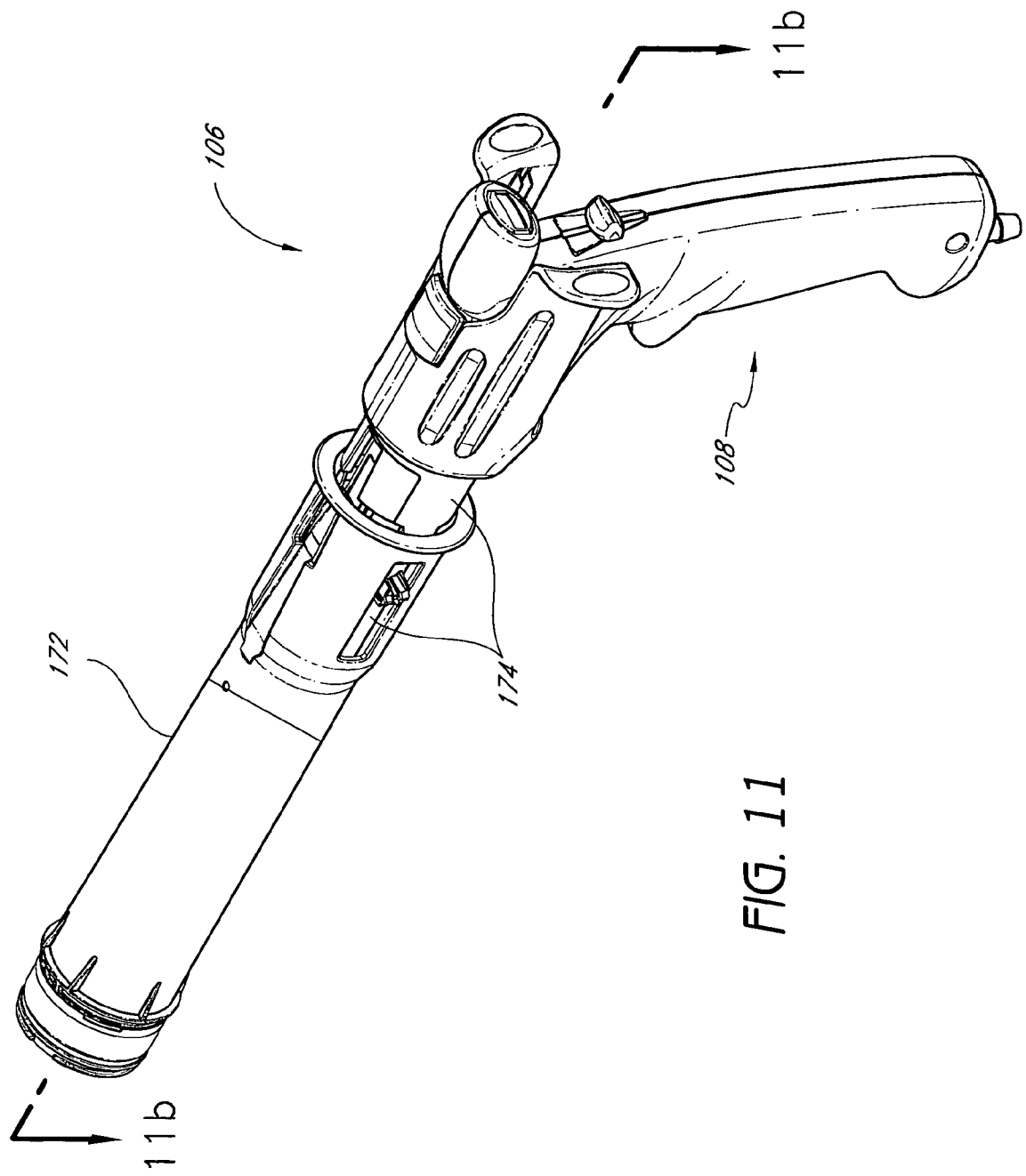
FIG. 11 is an assembled view of one embodiment of an introducing component and handle component.
Figure 11A:
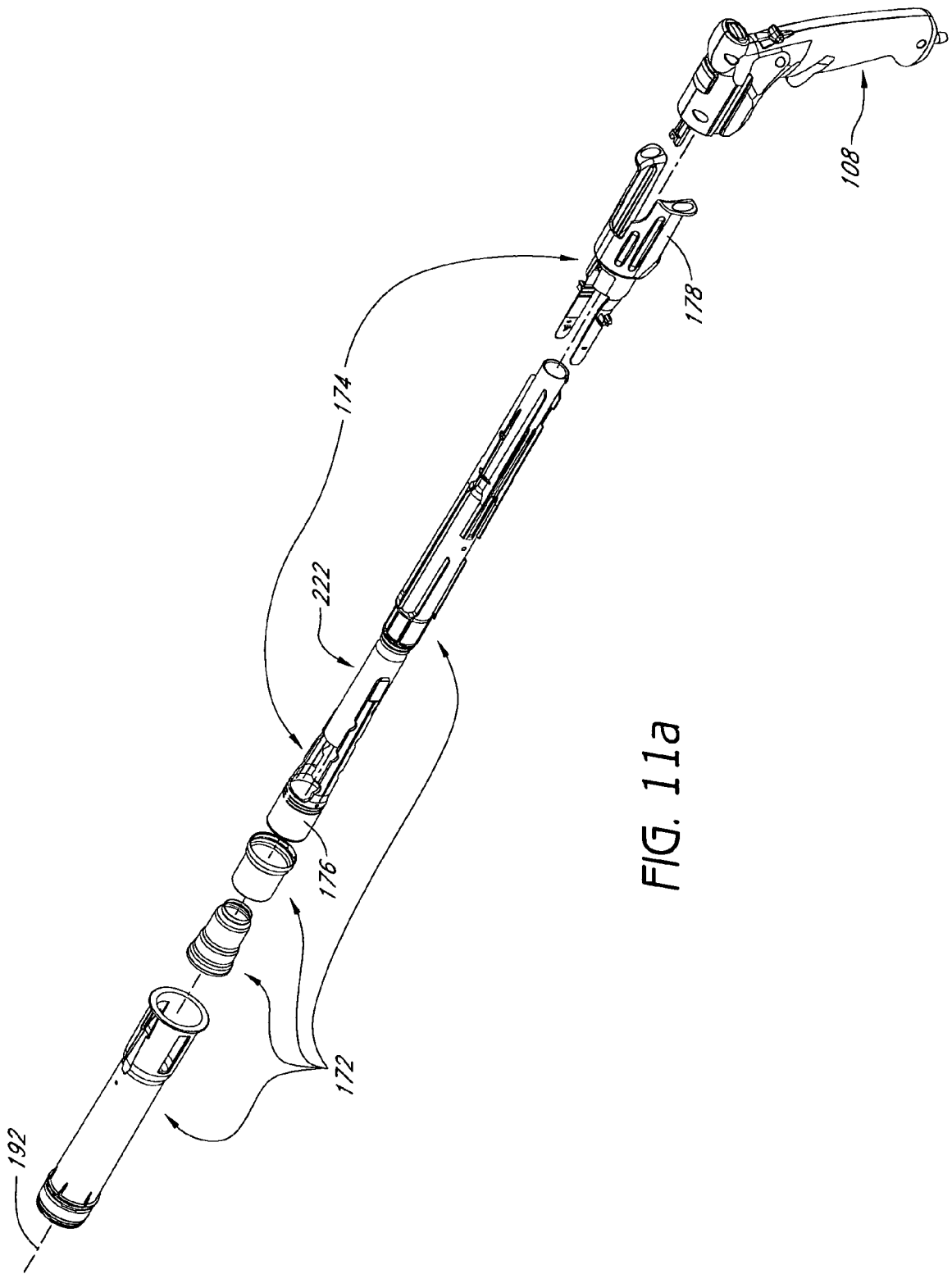
FIG. 11a is an exploded view of the introducing component and handle component of FIG. 11.

In the preferred embodiment, loading component 104 places resilient sleeve 100 on to introducing component 106 and prepares introducing component 106 to deploy resilient sleeve 100. Preferably, introducing component 106 retains resilient sleeve 100 in the expanded state until a user activates introducing component 106 to deploy resilient sleeve 100 on to a portion of body tissue. In this embodiment, introducing component 106 is comprised of an actuator 172, retainer 174, and friction liner 222. See FIGS. 11 and 11a. Axis 192 is the common axis of actuator 172 and retainer 174. The function of the introducing component in alternative embodiments of the invention may be accomplished by fewer or more parts.

Retainer

Figure 12:
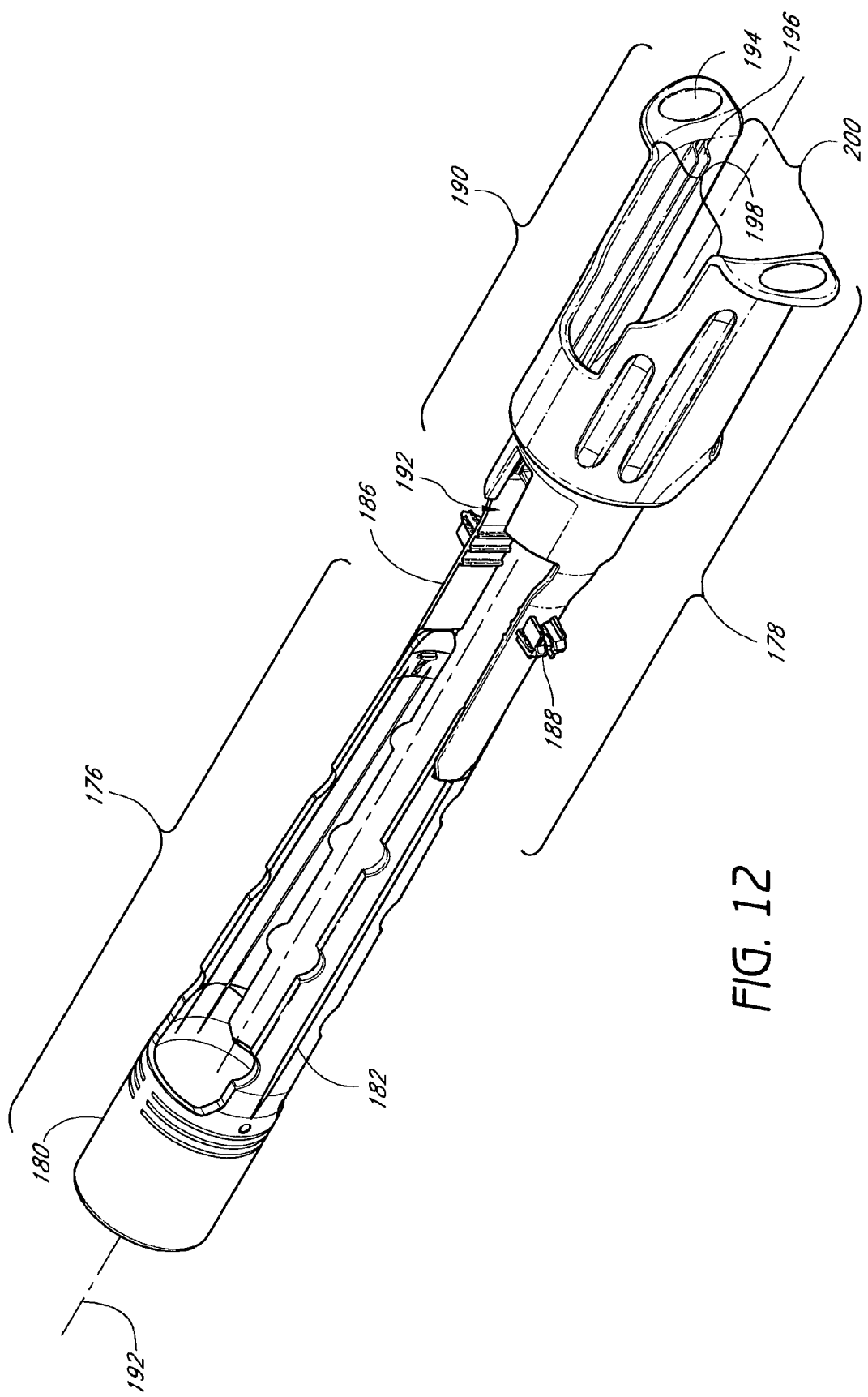
FIG. 12 is a perspective view of one embodiment of a retainer.
Figure 12A:
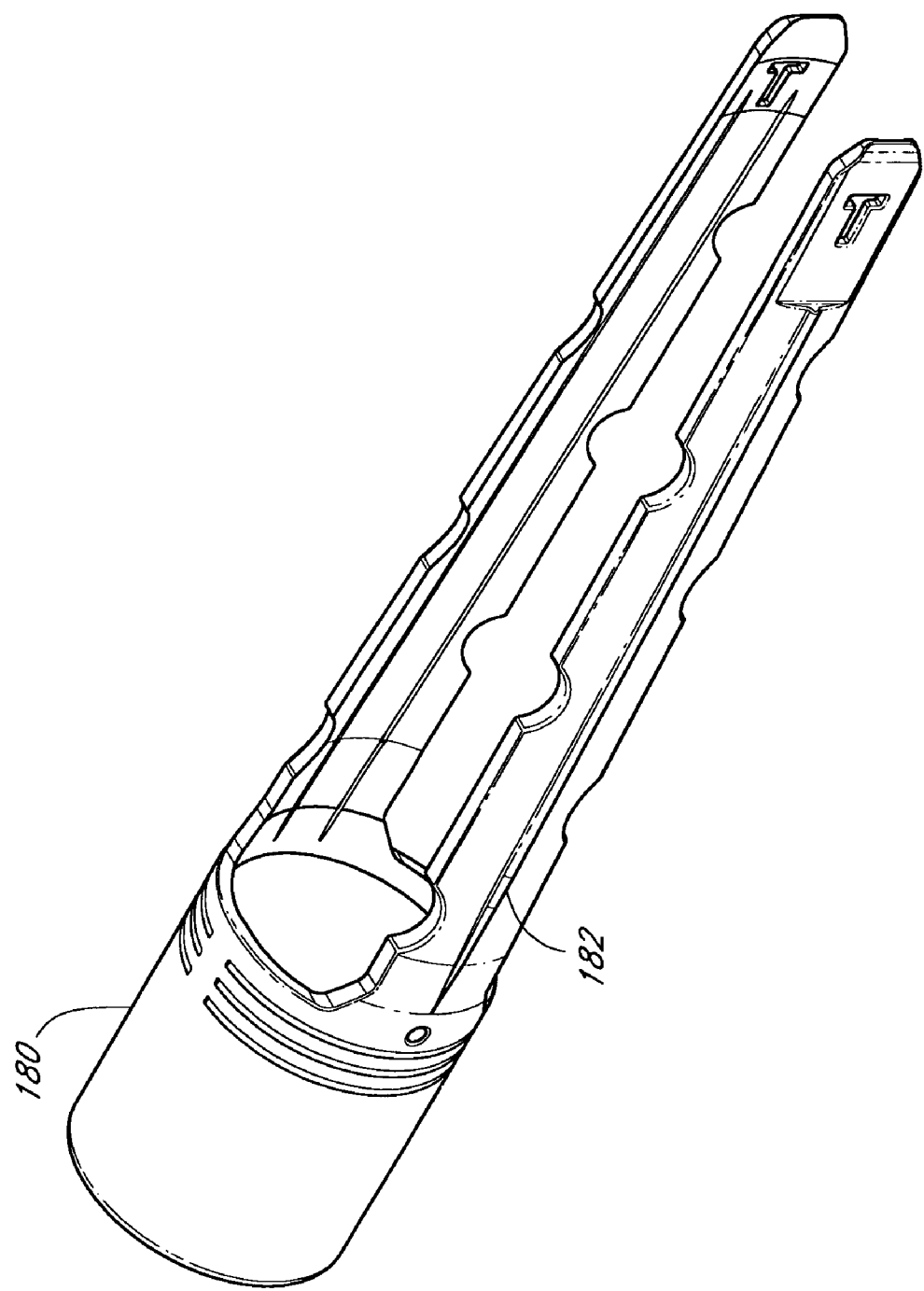
FIG. 12a is a perspective view of the distal portion of the retainer of FIG. 12.

In this embodiment of the invention, retainer 174 is generally of cylindrical shape and is comprised of a distal portion 176 and proximal portion 178. See FIG. 12. Distal portion 176 is comprised of a distal tip 180 and distal extenders 182, as shown in FIG. 12a. Proximal portion 178 is comprised of proximal extenders 186, channel tabs 188, and a proximal base 190. See FIG. 12b. Retainer 174 can be manufactured by shaping and/or cutting an extruded or molded plastic-type material such as polycarbonate. In alternative embodiments other material types and manufacturing methods may be utilized that are appropriate for constructing components of this type of medical device. It is also contemplated that the retainer may be constructed of one piece or more than two portions.

With reference to FIG. 12a, distal tip 180 is located at the distal most end of retainer 174 and is of continuous cylindrical shape. Preferably, two distal extenders 182 positioned diametric to each other extend proximally from the proximal end of distal tip 180 and are attached at their proximal end to the distal end of proximal extenders 186, as depicted in FIG. 12. Preferably, each distal extender 182 is a portion of a cylinder with an outer diameter roughly equal to the outer diameter of distal tip 180 and a width that increases slightly from their proximal to their distal end. See FIG. 12a.

In the preferred embodiment, proximal extenders 186 extend distally from the distal end of proximal base 190 and attach at their distal ends to the proximal ends of distal extenders 182. Preferably, proximal extenders 186 are of similar shape, size and diametric orientation as the proximal ends of distal extenders 182. A tab near the distal end of proximal extenders 186 is inserted into a slot at the proximal end of each distal extender 182 to connect distal extenders 186 to proximal extenders 186. See FIG. 12. Proximal and distal extenders may be of any suitable shape or orientation in alternative embodiments. In further embodiments, the function of distal and proximal extenders 182, 186 may be accomplished by other means, such as raised guides extending toward axis 192 from the inner surface of a retainer that is of continuous cylindrical shape as it extends proximally.

In this embodiment of the invention, a channel tab 188 is located on a longitudinal mid-portion of the outside surface of each proximal extender 186. Preferably, channel tabs 188 extend normal to the outside surface of retainer 174 away from axis 192. In this embodiment, channel tabs 188 are shaped and oriented such that they may reside within and travel through helical locking grooves 148 during the loading and positioning processes. See FIG. 12. In this embodiment also channel tabs 188 include lock notch 187 in which loader lock catch 170 resides to restrict relative movement between loading component 104 and introducing component 106. See FIG. 12.

In the preferred embodiment, proximal base 190 extend proximally from the proximal end of proximal extenders 186. Proximal base 190 may be cylindrical with a similar diameter as proximal extenders 186. The diameter of proximal base 190 may increase at an intermediary portion to accommodate insertion of handle component 108. See FIG. 12b. In this embodiment, proximal base 190 includes a distal cut-out 192, push ears or thumb wings 194, external handle guides 196, proximal upper cut-out 198, and a proximal lower cut-out 200.

Figure 12B:
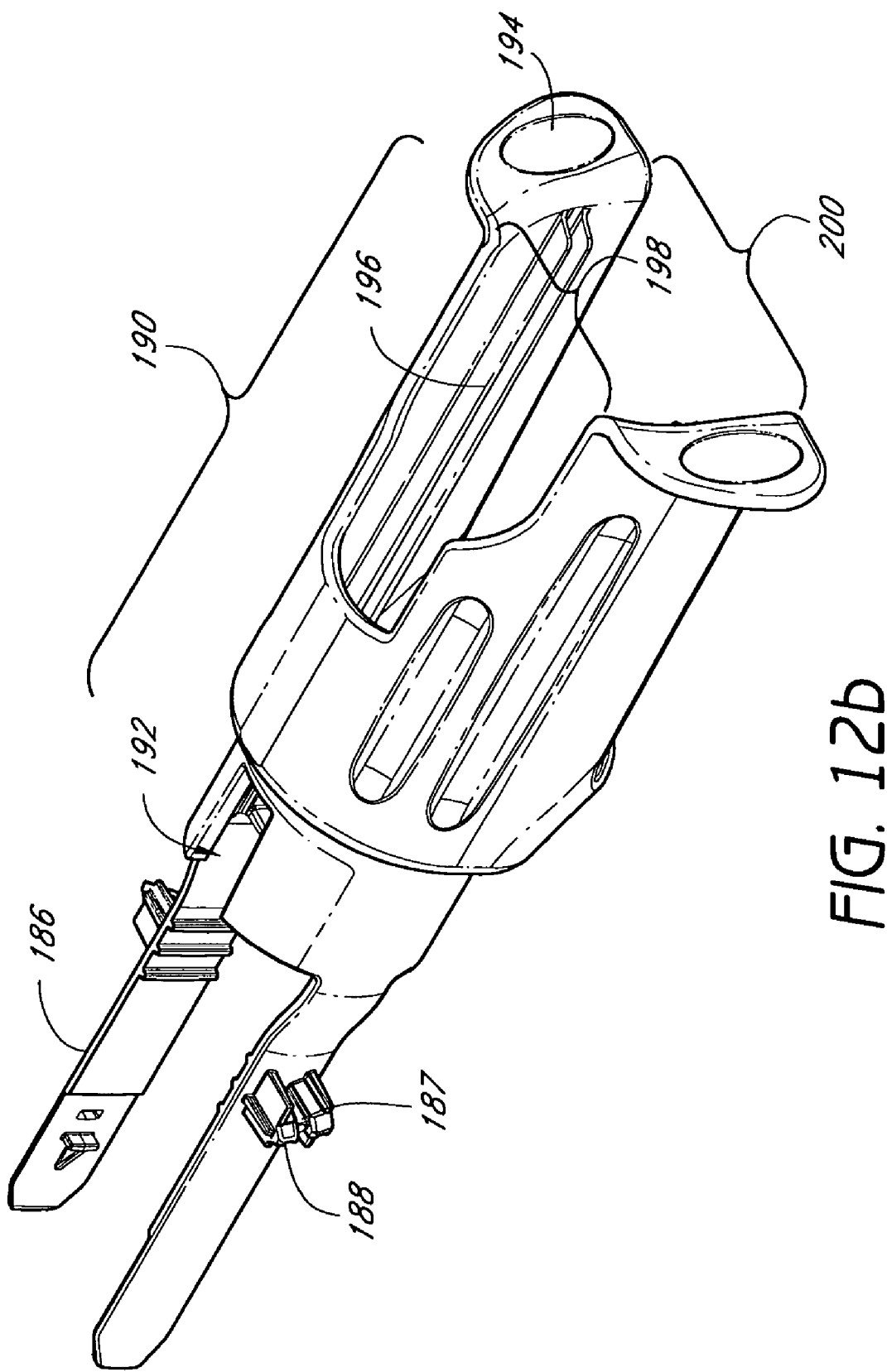
FIG. 12b is a perspective view of the proximal portion of the retainer of FIG. 12.
Figure 12C:
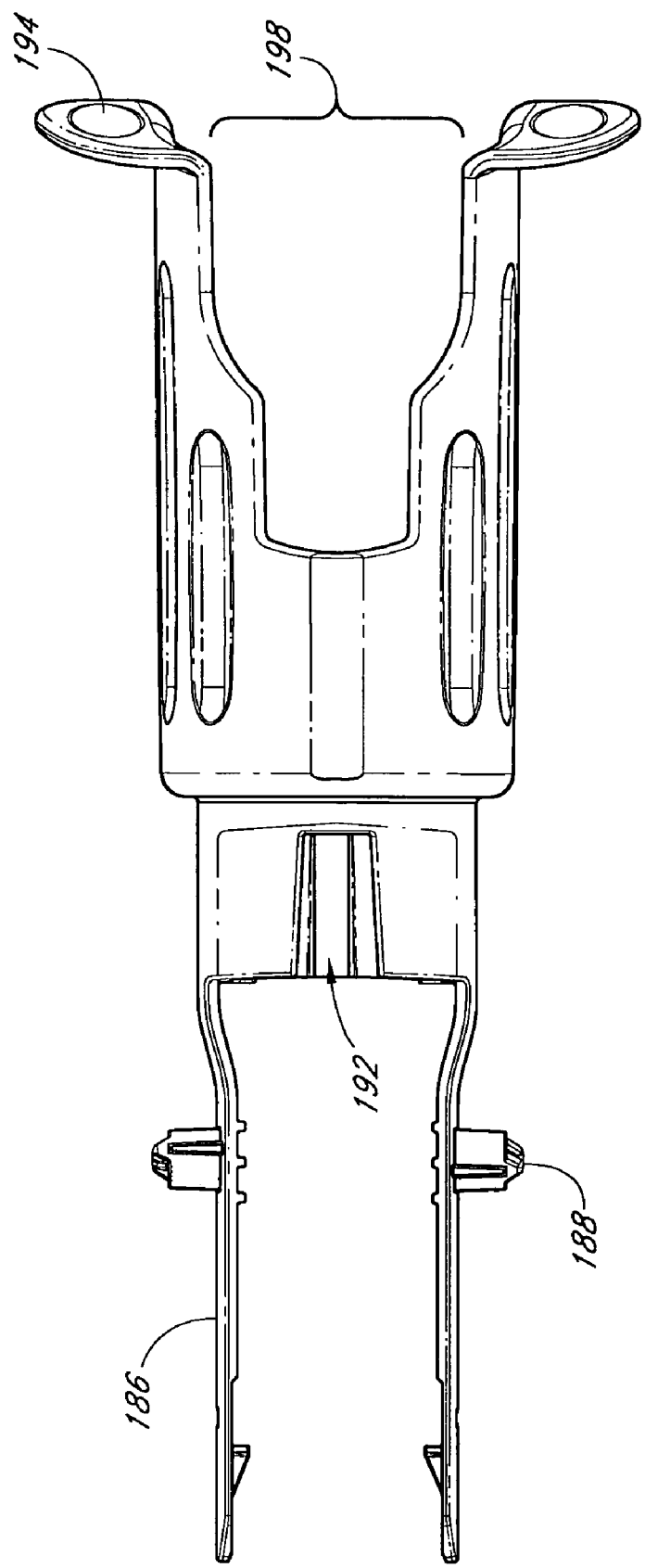
FIG. 12c is a top view of the proximal portion of the retainer of FIG. 12.

Preferably, distal cut-out 192 is approximately rectangular in shape and extends from an intermediate point along proximal base 190 through the distal end of proximal base 190. Preferably, distal cut-out 192 is oriented at the top of proximal base 190 at an equal distance along the diameter of proximal base 190 from where each proximal extender 186 meets proximal base 190, as shown in FIG. 12c. In other embodiments, distal cut-out 192 may be of any suitable shape and in any suitable location such that it provides clearance for lock release 232. Further, retainer 174 may be modified in other embodiments to eliminate the need for distal cut-out 192. For example, reducing the length of proximal base 190 and increasing the length of proximal extenders 186 would also provide clearance for lock release 232.

In the preferred embodiment, two push ears or thumb wings 194 are located at the proximal end of proximal base 190 and extend normal to and away from axis 192 at roughly diametric positions on a clock. Push ears or thumb wings 194 may have a slight oval shaped concave indentation on the proximal surface and may be configured with a slight distal angle from the bottom to top edge to provide a surface that is comfortable for a user's thumb to compress push ears or thumb wings 194, as illustrated in FIG. 12b. Push ears or thumb wings may be of any other suitable shape or orientation to allow a user to apply a distal force to retainer 174 during the loading and positioning processes.

On the internal surface of proximal base 190 in the preferred embodiment are external handle guides 196 that extend proximally from the point where the diameter of proximal base 190 increases to an intermediary point near the proximal end of proximal base 190. See FIG. 12b. Preferably, there are two external handle guides 196 positioned diametric to each other, each comprised of two raised walls extending radially inward. The distance between external surfaces of the raised walls of each external handle guide 196 may be such that external handle guides 196 can reside within external handle grooves 228 (part of handle component 108 and described below). In other embodiments, external handle guides may be of any other shape or size that adequately guides assembly and limits rotation between handle component 108 and introducing component 106. It is contemplated that the assembly of handle component 108 and introducing component 106 may be guided by other means.

Figure 12D:
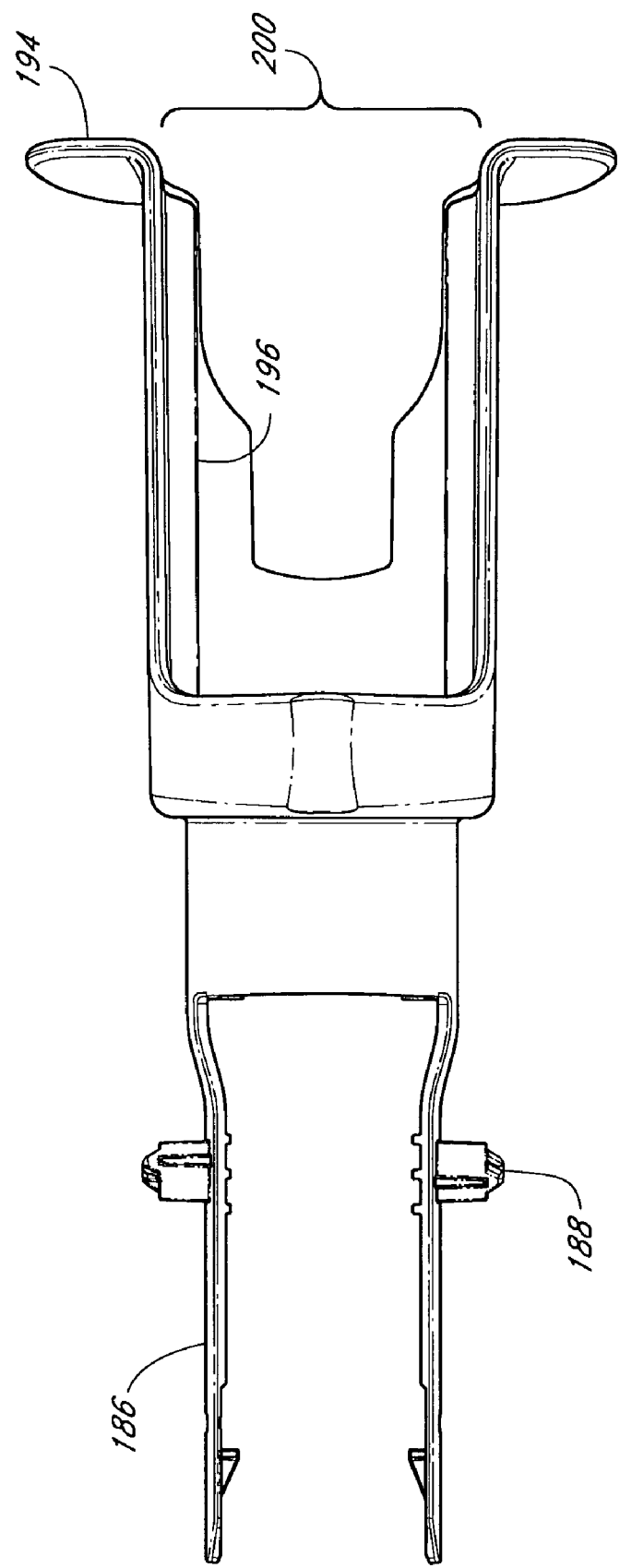
FIG. 12d is a bottom view of the proximal portion of the retainer of FIG. 12.

In the preferred embodiment, proximal lower cut-out 200 is roughly of rectangular shape and extends from an intermediary point through the proximal end of proximal base 190, as shown in FIG. 12d. Preferably, the proximal upper cut-out 198 also extends from an intermediary point through the proximal end of proximal base 190. See FIG. 12c. The intermediary point may not be the same for the two cut-outs (198, 200). The size and shape of proximal lower cut-out 200 and proximal upper cut-out 198 is appropriate to accommodate insertion of handle component 108 and provide access to handle a release button 238 located on handle component 108. In other embodiments, the proximal cut-outs (198, 200) may be of different shape or location than those described or depicted or may not be present at all.

Actuator

Figure 13:
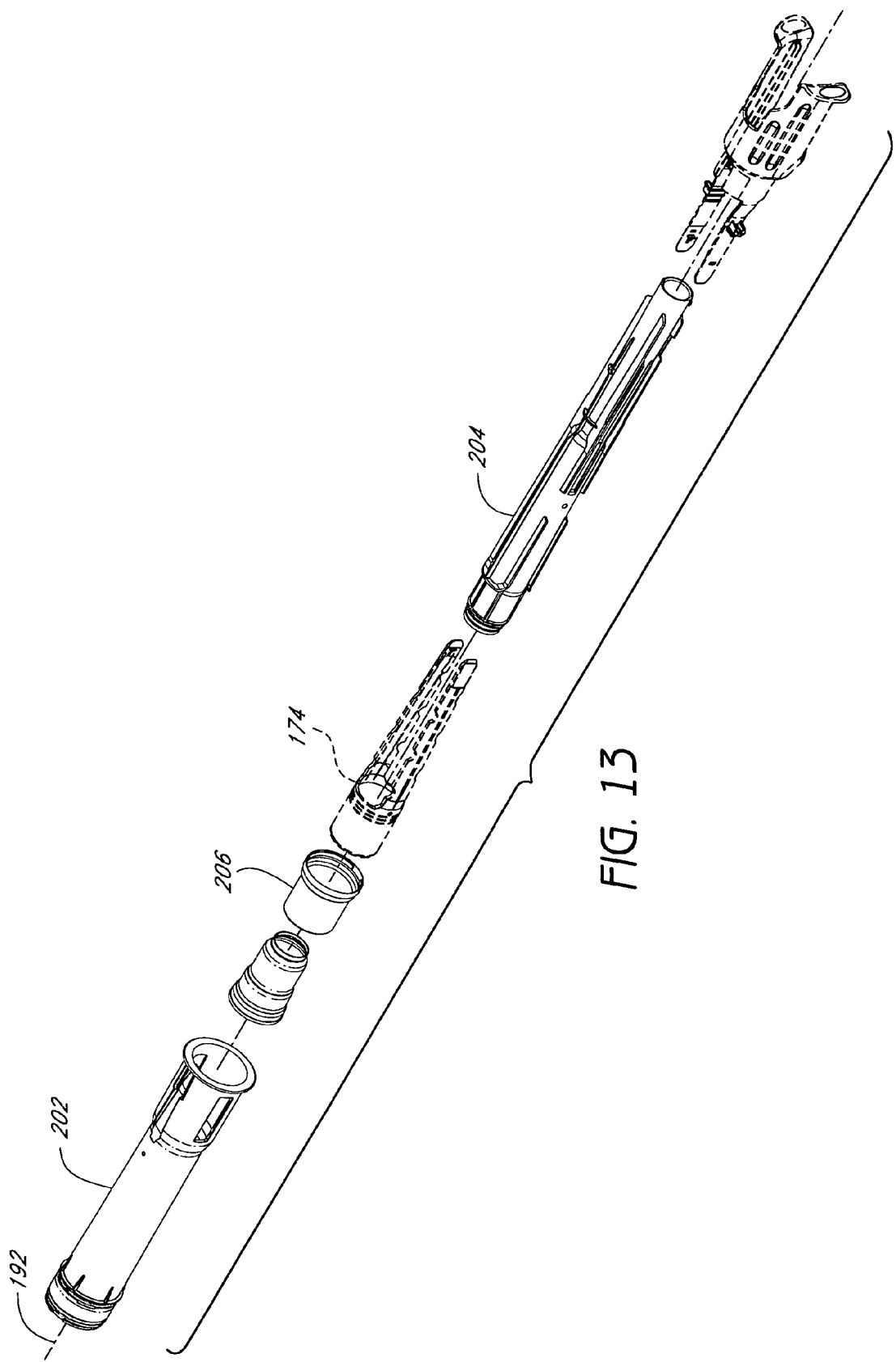
FIG. 13 is an exploded view of one embodiment of an actuator.

Some functions of actuator 172 are to re-position resilient sleeve 100, lock introducing component 106 when resilient sleeve 100 is properly positioned, and deploy resilient sleeve 100. In this embodiment, actuator 172 is comprised of an actuating cylinder 202, locking cylinder 204, and sleeve guide 206, as illustrated in FIG. 13. Preferably, actuating cylinder 202 is concentrically external to the portion of retainer 174 that is of smaller diameter, and locking cylinder 204 is concentrically internal to retainer 174. See FIG. 13. Actuating cylinder 202 and locking cylinder 204 may be shaped and/or cut from an extruded or molded plastic-type material such as polycarbonate. Any other suitable material or manufacturing method may also be utilized. Advantageously, polycarbonate provides a durable material that facilitates manufacturing and assembly and is safe for a medical device of this type.

Figure 14:
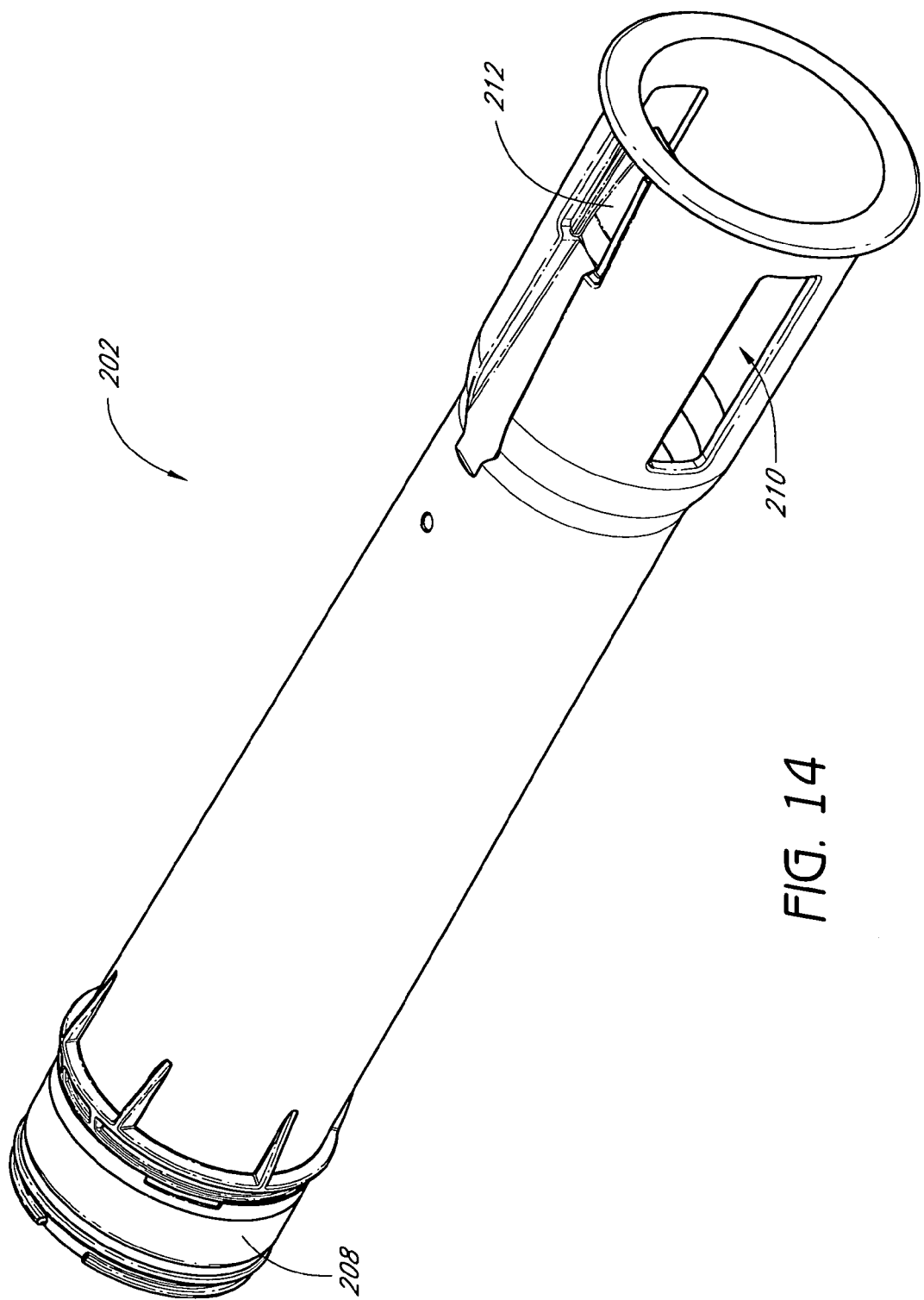
FIG. 14 is an assembled view of one embodiment of the actuating cylinder.

In the preferred embodiment of the invention, actuating cylinder 202 includes a compression cap 208, slots 210, and locking tab 212. See FIGS. 14 and 14a. Preferably, compression cap 208 is located at a distal end of actuating cylinder 202. The inner diameter of compression cap 208 may be large enough to so that relative axial movement between actuating cylinder 202 and retainer 174 is not encumbered. Preferably, compression cap 208 includes a compression groove 213 formed by two walls 215, 217 extending outward from and near the distal end of the outer surface of compression cap 208. Preferably, compression tabs 153 reside within this groove during the loading process. The diameter of walls 215, 217 may be greater than the inner diameter of compression tabs 153 but not so large as to encumber relative axial movement between loading component 104 and introducing component 106. Preferably, tab release gaps 211 are placed around wall 217 that are of greater width than compression tabs 153. Tab release gaps 211 may be of slightly smaller diameter than the diameter formed by the inner diameter of compression tabs 153. There may the same number of tab release gaps 211 as there are compression tabs 153. In alternative embodiments, the compression groove and tab release gaps may not be present. For example, compression tabs 153 could make direct contact with the distal end of compression cap 208. Desirably, compression cap 208 is constructed by shaping an extruded or molded plastic-type material such as polypropylene. In alternative embodiments other material types and manufacturing methods may be utilized that are appropriate for constructing components of this type of medical device.

Desirably, actuating cylinder 202 is constructed by shaping and/or cutting an extruded or molded plastic-type material such as polycarbonate. In alternative embodiments other material types and manufacturing methods may be utilized that are appropriate for constructing components of this type of medical device. In this embodiment, there are two slots 210 of approximately rectangular shape located diametric to each other and oriented longitudinally on actuating cylinder 202, as shown in FIG. 14a. Preferably, the width of slots 210 is slightly wider than the width of channel tabs 188. Channel tabs 188 may protrude through slots 210 to limit relative rotation between actuating cylinder 202 and retainer 174 and limit relative axial movement between the same components to the length of slots 210. It is contemplated that limiting relative movement between actuating cylinder 202 and retainer 174 may be accomplished by alternative means. Channel tabs 188 of the preferred arrangement are preferred because they also cooperate with loading component 104 during the loading and positioning processes.

In the preferred embodiment, locking tab 212 extends proximally from a portion distal the proximal end of actuating cylinder 202 at an angle towards axis 192 and has a tab ramp 214 at its proximal end. SEE FIGS. 14b and 14c. Locking tab 212 may be biased toward axis 192 such that it cooperates with locking catch 216 (located on locking cylinder 204) to limit relative axial movement between actuating cylinder 202 and locking cylinder 204 when the apparatus is prepared to deploy resilient sleeve 100.

Locking Cylinder

Figure 15:
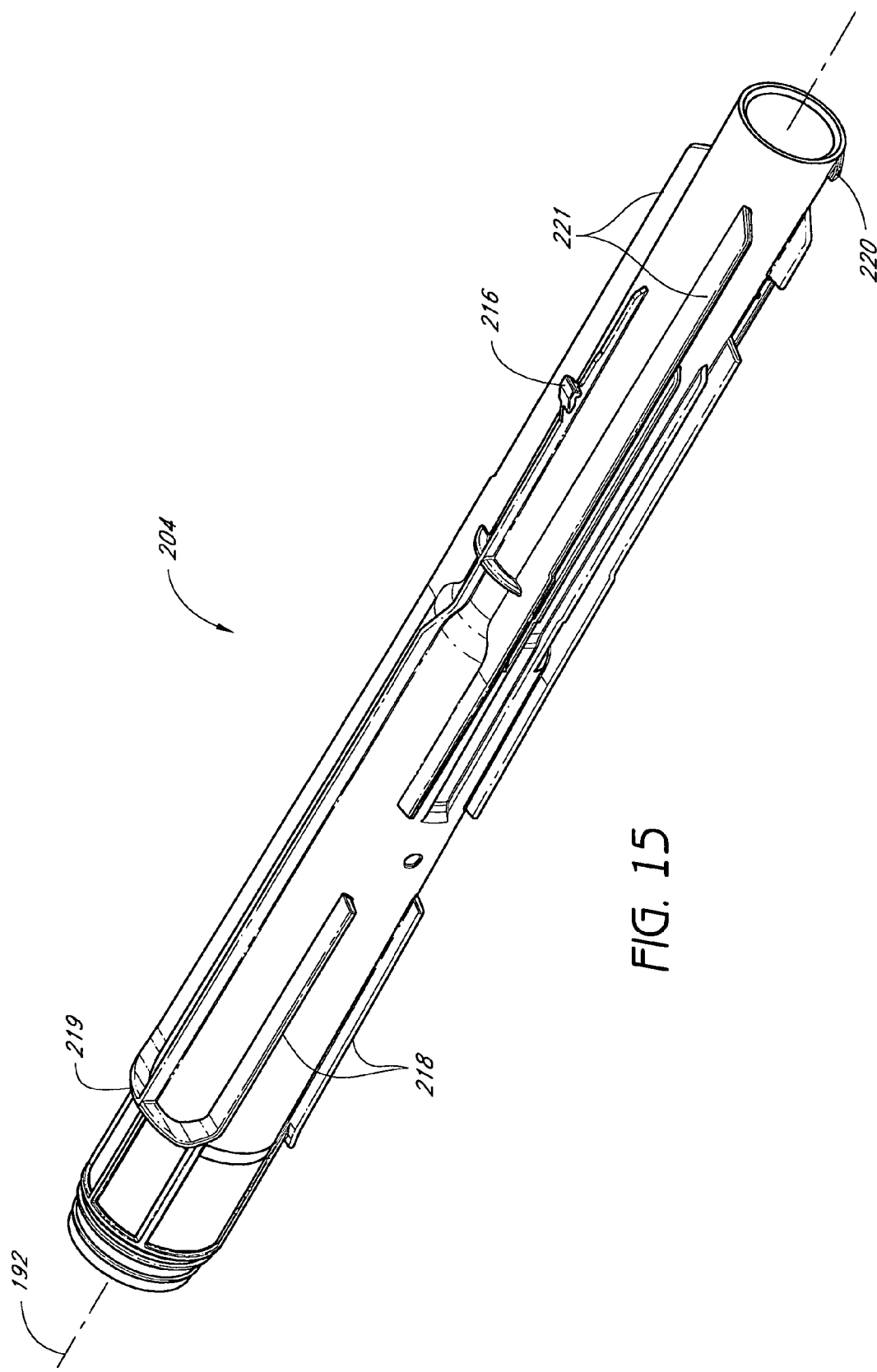
FIG. 15 is a perspective view of one embodiment of a locking cylinder.

In the preferred embodiment, locking cylinder 204 includes a locking catch 216, raised grooves 218, raised lips 219, handle tab 220 and friction liner 222, as shown in FIG. 15. A distal portion of locking cylinder 204 may be of greater diameter than a proximal portion. Desirably, locking cylinder 204 is constructed by shaping and/or cutting an extruded or molded plastic-type material such as polycarbonate. In alternative embodiments other material types and manufacturing methods may be utilized that are appropriate for constructing components of this type of medical device.

Preferably, locking catch 216 protrudes away from axis 192 from the outside surface of locking cylinder 204 and includes a catch ramp 224. See FIGS. 15 and 15a. Locking catch 216 may be oriented at the top of and at a point distal the proximal end of locking cylinder 204 such that it resides within distal cut-out 192 of retainer 174 and aligns radially with locking tab 212 of actuating cylinder 202. See FIG. 14c. Preferably, locking catch 216 aligns axially with locking tab 212 such that it prevents relative axial movement between locking cylinder 204, actuating cylinder 202, and retainer 174 when introducing component 106 is locked and prepared to deploy resilient sleeve 100. In other embodiments, axial movement can be limited by other means, such as a rotating clasp or a slidable lock. An advantage of the preferred embodiment is that locking tab 212 engages locking catch 216 when actuating cylinder 202 is moved proximally by the rotation of retractor 114. The user need simply to rotate retractor 114 to engage locking tab 212 to locking catch 216, which simplifies the loading process and reduces the operations a user must perform.

In the preferred embodiment of the invention, proximal and distal extenders (182, 186) reside within raised grooves 218 to limit relative rotation between retainer 174 and locking cylinder 204. Each raised groove 218 in this embodiment is formed by two walls extending away from axis 192 from the outer surface of locking cylinder 204. See FIG. 15. Each raised groove 218 may have a proximal and distal portion, the two walls being parallel with respect to each other in the proximal portion and non-parallel with respect to each other in the distal portion. The proximal portion of the first groove 218 may be formed by a first wall that is oriented horizontally above and axis 192 and a second that is oriented horizontally and below axis 192. The proximal portion of second groove 218 may be formed by two walls also extending from the outers surface of locking cylinder 204 that are respectively co-planar to the first and second walls of first groove 218 but extend in the opposite direction. See FIG. 15b. In the preferred embodiment the distance between the walls forming the proximal portion of each raised groove 218 is slightly greater than the width of proximal extenders 186. The proximal portion of raised grooves 218 also functions as internal handle guides 221, as described below. In the distal portion of raised grooves 218 the walls forming each raised groove 218 diverge from each other such that the distance between the walls increases approaching the distal end and remains slightly greater than the increasing width of distal extenders 186. In the preferred embodiment, two raised lips 219 are formed between the distal ends of first and second raised grooves 218, as depicted in FIGS. 15 and 15a. In alternative embodiments, the raised grooves may be of different shape or orientation, or their function may be accomplished by other suitable means. For example, relative rotation between retainer 174 and locking cylinder 204 may be limited by tabs on locking cylinder 204 that extend through or engage with slots in the wall of retainer 174. In other embodiments, proximal and distal extenders (182, 186) may reside in channels cut into the wall of locking cylinder 204. Raised grooves 218 are advantageous because they also serve as internal handle guides 221, which provides for ease and efficiency in manufacturing.

In the preferred embodiment, handle tab 220 extends radially away from axis 192 from the proximal end of the outer surface of locking cylinder 204 to an intermediate portion thereof. See FIG. 15b. Handle tab 220 cooperates with handle catch 240 to secure handle component 108 to locking cylinder 204. Handle tab 220 may be oriented along a bottom portion of the outer diameter of locking cylinder 204 (location of locking catch 216 being the top of locking cylinder 204). Handle tab 220 may be configured such that the distance it extends away from the outer surface of locking cylinder 204 increases from its proximal to distal end to form a ramp-like feature. In alternative embodiments, handle tab 220 may be of different shape or orientation, or handle component can be secured to locking cylinder 204 in a different manner. The preferred embodiment of handle tab 220 provides ease of assembly and disassembly between introducing component 106 and handle component 108.

Sleeve guide 206 is preferably of cylindrical shape and constructed of a resilient material. Sleeve guide 206 may be attached at one end to the distal end of the outer surface of actuating cylinder 202 (under compression cap 208) and at the other end to the distal end of the outer surface of locking cylinder 204. FIG. 13 shows sleeve guide 206 disassembled from actuator 172. As retainer 174 is located concentrically internal to actuating cylinder 202 and concentrically external to locking cylinder 204, sleeve guide 206 encases the distal end of retainer 174 in this configuration by connecting the distal ends of actuating cylinder 202 and locking cylinder 204. Sleeve guide 206 allows relative axial movement between retainer 174 and resilient sleeve 100 during the positioning and releasing processes (described below). Preferably, a piece of fabric of similar shape to sleeve guide 206 is placed along the inner surface of sleeve guide 206. The fabric limits friction between sleeve guide 206 and retainer 174 during the loading, positioning, and release processes.

Loading Process

As described above, continued rotation of retractor 114 in this embodiment releases loader locks 142, which permits relative movement between loading component 104 and introducing component 106. A distal force is applied to push ears 194 to ensure that retainer 174 remains in a distal most position and is tensely encased by sleeve guide 206 during loading. Because relative movement between retractor 114 and guide cylinder 112 is restricted by securing recesses 146 at this point in the loading process, continued rotation of retractor 114 causes relative movement between loading component 104 and introducing component 106. Preferably, the relative movement is guided by channel tabs 188 traveling through locking grooves 148, which cooperate to move loading component 104 proximally relative to introducing component 106. As loading component 104 moves proximally, compression tabs 153 contact the wall 215 of compression cap 208, causing actuating cylinder 202 to move proximally relative to retainer 174 and locking cylinder 204. Proximal movement of actuating cylinder 202 exposes the distal end of retainer 174 (encased by sleeve guide 206), providing a surface on which resilient sleeve 100 may be loaded. In other embodiments, the function of the compression tabs 153 may be achieved by varying the length of guide cylinder 112 or by any other suitable design. Advantageously, two compression tabs 153 are a simple and easily manufactured design that firmly and uniformly compress actuating cylinder 202 during the expansion process.

Positioning Process

Because sleeve guide 206 encases retainer 174 between actuating cylinder 202 and locking cylinder 204, sleeve guide 206 pulls locking cylinder 204 distally relative to retainer 174 as actuating cylinder 202 is compressed proximally. Upon continued rotation of retractor 114, the relative proximal movement of actuating cylinder 202 pulls sleeve guide 206 and resilient sleeve 100 proximally relative to retainer 174. As resilient sleeve 100 is drawn proximally on retainer 174, the interior of the distal portion of resilient sleeve 100 is exposed. Actuating cylinder 202 (and therefore sleeve guide 206 and resilient sleeve 100) moves proximally relative to locking cylinder 204 and retainer 174 until tab ramp 214 (located on actuating cylinder 202) meets and engages catch ramp 224 (located on locking cylinder 204). Relative movement between actuating cylinder 202, locking cylinder 204, and retaining cylinder 174 is now limited. Further, in the preferred embodiment, each feature is dimensioned such that when tab ramp 214 engages catch ramp 224, raised lips 219 are pressed firmly against the proximal edge of distal tip 180, sleeve guide 100 is stretched taught between actuating cylinder 202 and locking cylinder 204 encasing the distal end of retainer 174, and resilient sleeve 100 is fully prepared for deployment.

Both the loading and positioning processes are accomplished by the continued rotation of retractor 114 ("simple twist"). The "simple twist" of retractor 114 expands, loads and positions resilient sleeve 100 such that it is fully prepared to be deployed on to body tissue. As discussed above, the "simple twist" feature provides ease of operation for users of the invention and promotes efficiency in medical procedures in which the invention is used.

Preferably, the relative rotation between loading component 104 and introducing component 106 caused by the "simple twist" of retractor 114 also aligns compression tabs 153 with tab releases 211 and channel tabs 188 with release channels 150 when the device is fully prepared to deploy resilient sleeve 100. This allows an operator to separate loading component 104 from introducing component 106 by sliding loading component 104 distally relative to introducing component 106

Handle Component

Figure 16A:
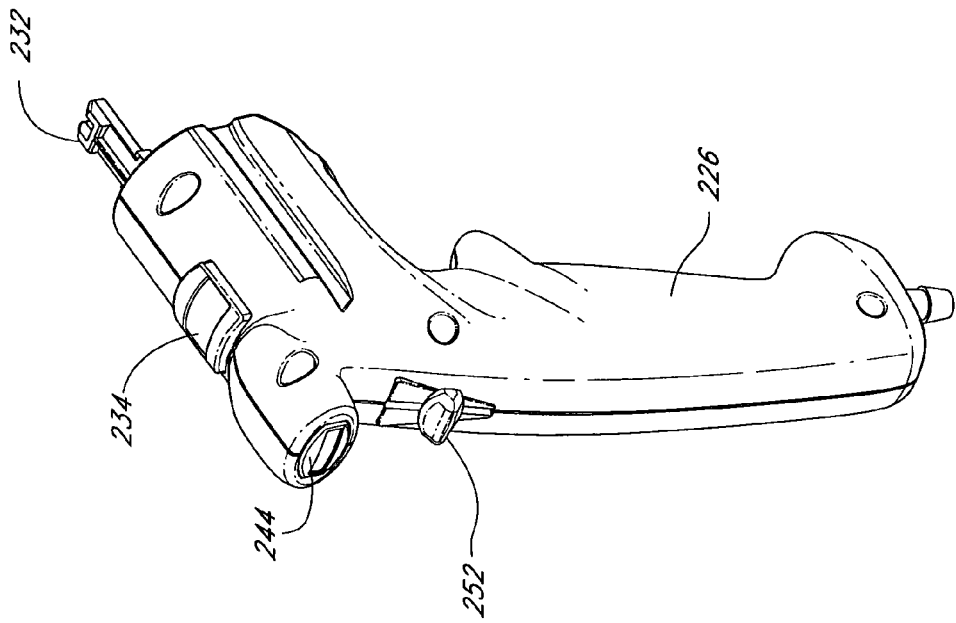
FIG. 16a is a perspective view of the other side of the handle component of FIG. 16.
Figure 16:
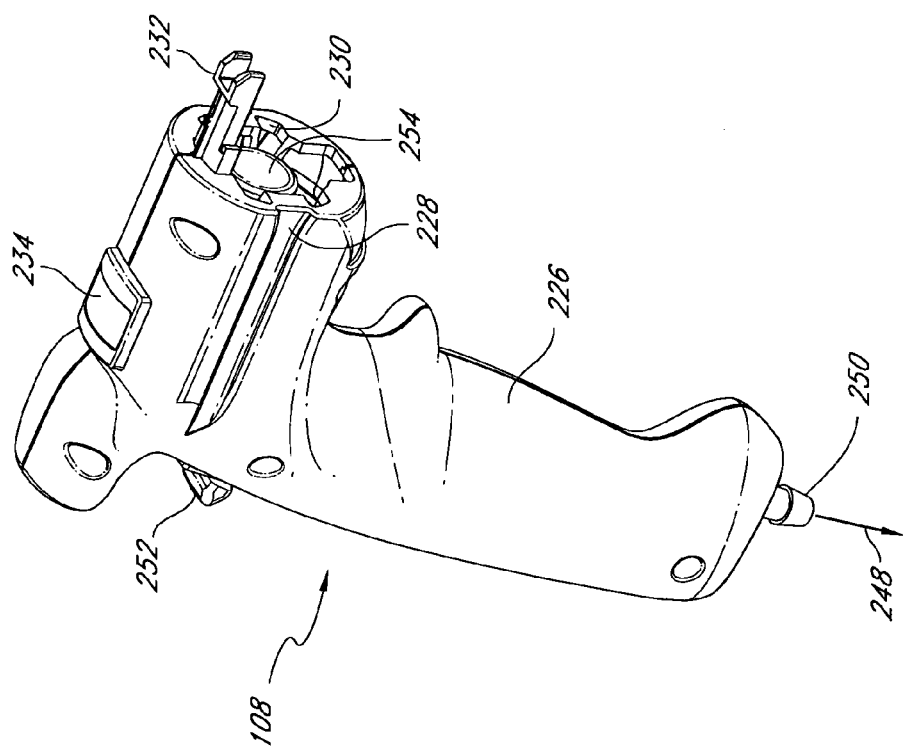
FIG. 16 is a perspective view of one embodiment of a handle component.

In the preferred embodiment, handle component 108 is comprised of a handle 226, external handle grooves 228, internal handle grooves 230, lock release 232, handle latch 234, and a vacuum system, as depicted FIGS. 16 and 16a, and may be such that a user can ergonomically grasp handle 226, adjust vacuum lever 252, and operate handle latch 234 with a single hand. Handle 226 may be constructed in two halves to facilitate manufacturing and assembly. Preferably handle 226 is constructed by molding a plastic-type material such as polycarbonate. Other material types and manufacturing methods may be utilized that are appropriate for constructing components of this type of medical device.

In the preferred embodiment, handle component 108 is detachable from introducing component 106. Preferably, handle component 108 is attached to introducing component 106 by inserting handle component through the proximal end of proximal base 190. Preferably, a distal portion of handle component 108 resides within proximal base 190 when handle component 108 is combined with introducing component 106. External handle grooves 228 and internal handle grooves 230 align handle component 108 with introducing component 106 when the components are combined. The same features prevent relative rotation between introducing component 106 and handle component 108. External handle grooves 228 may be configured and orientated on the outside surface of handle 226 such that they receive external handle guides 196 (located on retainer 174) when handle component 108 is combined with introducing component 106. See FIG. 16. Internal handle grooves 230 may be located and oriented on the internal surface of handle 226 such that they receive internal handle guides 221 when handle component 108 is combined with introducing component 106. Any other suitable method may be used to align, guide and prevent relative rotation between introducing component 106 and handle component 108. In further embodiments, it is not required that the assembly of introducing component 106 and handle component 108 may is guided or aligned. These components may also be free to rotate relative to each other. Additionally, introducing component and handle component may be permanently combined.

Figure 16B:
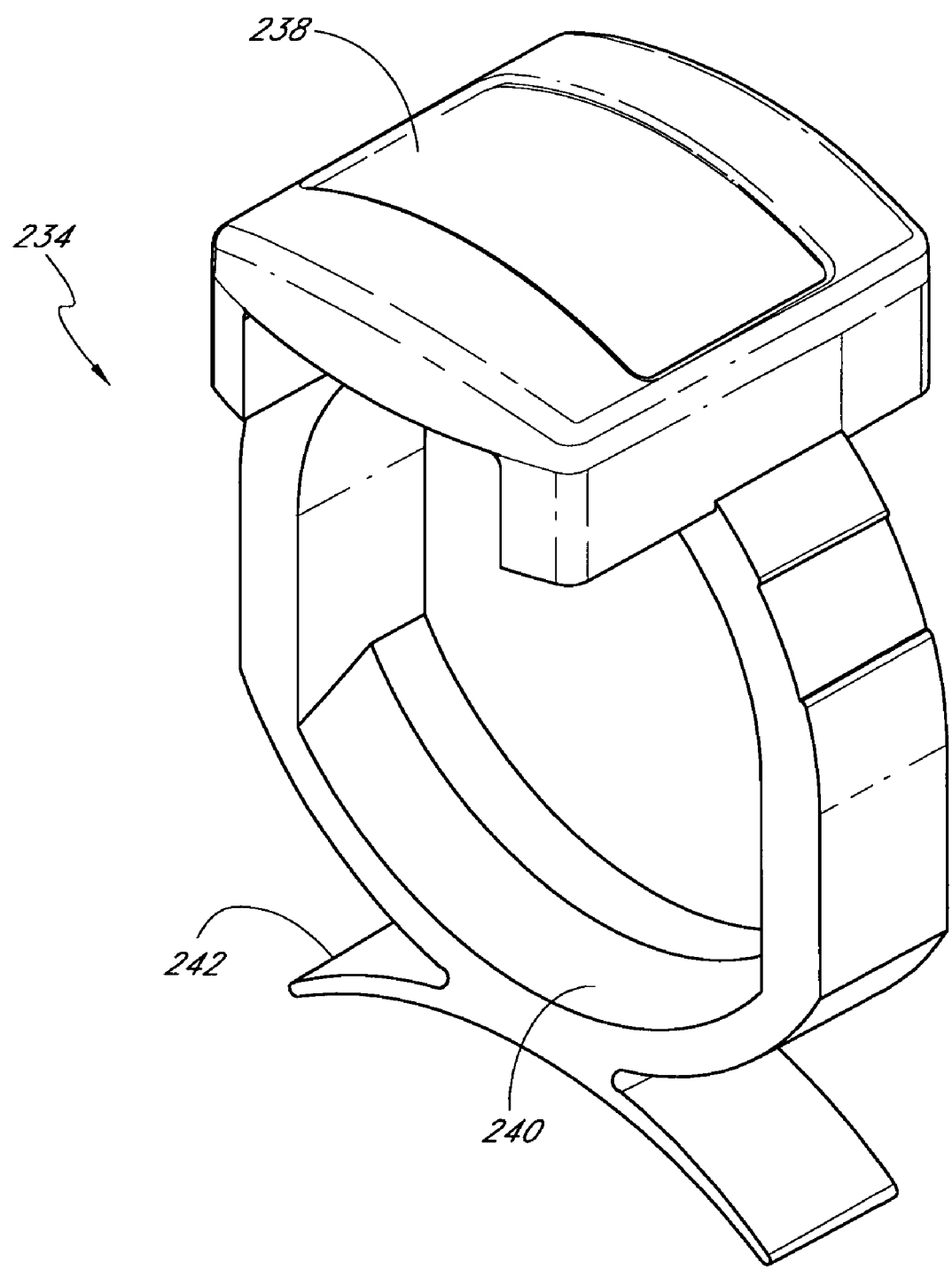
FIG. 16b is a perspective view of one embodiment of a handle release.

Preferably, handle latch 234 cooperates with handle tab 220 to limit relative axial movement between handle component 108 and locking cylinder 204 when handle component 108 is combined with introducing component 106. In this embodiment, handle latch 234 includes a handle release button 238, handle catch 240 and latch spring 242, as shown in FIG. 16b. Accordingly, when handle component 108 is inserted into introducing component 106, handle tab 220 contacts handle catch 240 thereby compressing latch spring 242. When handle component 108 is completely assembled with introducing component 106, handle tab 220 extends through handle latch 234. This allows latch spring 242 to rebound from its compressed state, such that a distal surface of handle tab 220 is secured by a proximal surface of handle latch 234. This limits relative axial movement between handle component 108 and locking cylinder 204.

Figure 16C:
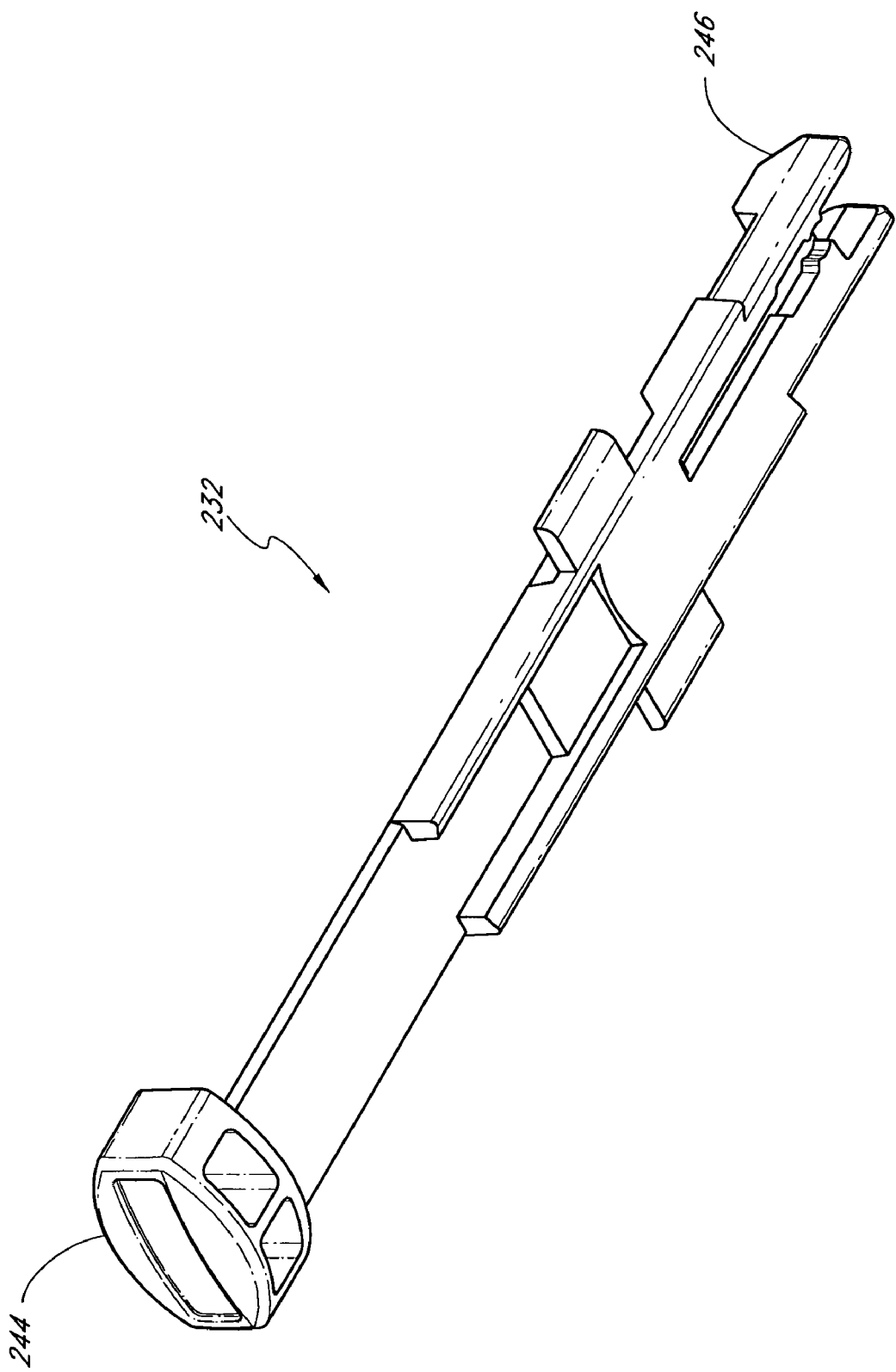
FIG. 16c is a perspective view of one embodiment of a lock release.

In the preferred embodiment of the invention, lock release 232 includes a lock release button 244 at a proximal end and lock release ramp 246 at a distal end. See FIG. 16c. Lock release 232 may be located near the top of handle 226 (as shown in FIG. 16a) such that it is roughly at the same radial orientation and distance from axis 192 as tab ramp 214 when handle component 108 is combined with introducing component 106. See FIG. 16. Lock release 232 may extend through both ends of handle 226 approximately parallel to axis 192 (when handle component 108 is combined with introducing component 106) such that lock release button 244 is proximal to handle 226 and lock release ramp is distal to handle 226. The length of lock release 232 may be such that lock release ramp 246 extends slightly past tab ramp 214 when handle component is combined with introducing component 106.

In the preferred embodiment, when actuating cylinder 202 moves proximally relative to locking cylinder 204 and catch ramp 224 engages tab ramp 214 (i.e. during the Positioning Process), catch ramp 224 contacts lock release ramp 246 and moves lock release 232 proximally relative to locking cylinder 204. Lock release ramp 246 may be proximal relative to tab ramp 214 and slightly below catch ramp 224 when locking tab 212 is engaged with locking catch 216.

Vacuum System

The vacuum system operates to draw the body tissue within the confines of resilient sleeve 100 before resilient sleeve 100 is released from retainer 174. In the preferred embodiment of the invention, the vacuum system includes a vacuum source 248, vacuum fitting 250, vacuum lever 252 and vacuum tubing 254. See FIG. 16. Vacuum source 248 may be any system that is capable of drawing vacuum through 250. Preferably, vacuum fitting 250 is attached to the bottom of handle 226 and provides a secure connection between handle component and vacuum source 248. Vacuum fitting 250 may be barbed on one end to securely connect a tube originating from vacuum source 248. In this embodiment, vacuum lever 252 provides regulation of the vacuum strength applied to the targeted body tissue. Vacuum lever 252 may be a vertically slidable switch located on the proximal edge of handle 226 such that the thumb of the hand grasping the handle can be used to adjust the vacuum.

It is contemplated that the vacuum system may be connected at any suitable location on introducing component 106. Alternative embodiments may use other suitable means, such as forceps or other devices, to pull the body tissue into resilient sleeve 100. Advantageously, a vacuum system provides a continuous and adjustable source of suction for which direct contact with sensitive body tissue is unnecessary.

Release Process

In the preferred embodiment, depressing lock release button 244 causes lock release ramp 246 to lift and move tab ramp 214 proximally, releasing locking tab 212 from locking catch 216 thereby permitting relative axial movement between actuating cylinder 202, retainer 174, and locking cylinder 204. See FIGS. 11b and 11c. An operator may now release resilient sleeve 100 to constrict on targeted body tissue by compressing push ears 194 distally. The distal force on push ears 194 ensures that sleeve guide 206 tensely encases retainer 174 while actuating cylinder 202 moves distally relative to retainer 174 and locking cylinder 204, and locking cylinder moves proximally relative to retainer 174. Relative movement between sleeve guide 206 and retainer 174 causes resilient sleeve 100 to move distally relative to retainer 174 until it is released from the distal end of retainer on to targeted body tissue.

"Simple twist" is not a required feature for this invention. Alternative embodiments may provide different means of expanding, loading, and positioning resilient sleeve 100 and preparing the apparatus to deploy resilient sleeve 100. For example, a "shot-gun" style design may be employed in which the single act of pulling an actuator proximally performs all of these functions. Additionally, the invention may be configured such that the simultaneous squeeze and pull of an actuator performs these functions. In the "squeeze and pull" embodiment, levers may be hinged to each other at an intermediate portion such that compressing a proximal portion of the levers expands a distal portion of the levers. Furthermore, the levers may not be hinged and may operate independently. For example, the levers may be biased inward at the distal end and have a common pivot at an intermediary portion such that squeezing the proximal ends expands the distal ends. It is also contemplated that other designs not mentioned here may be used in place of the "simple twist" feature.

Figure 1A:
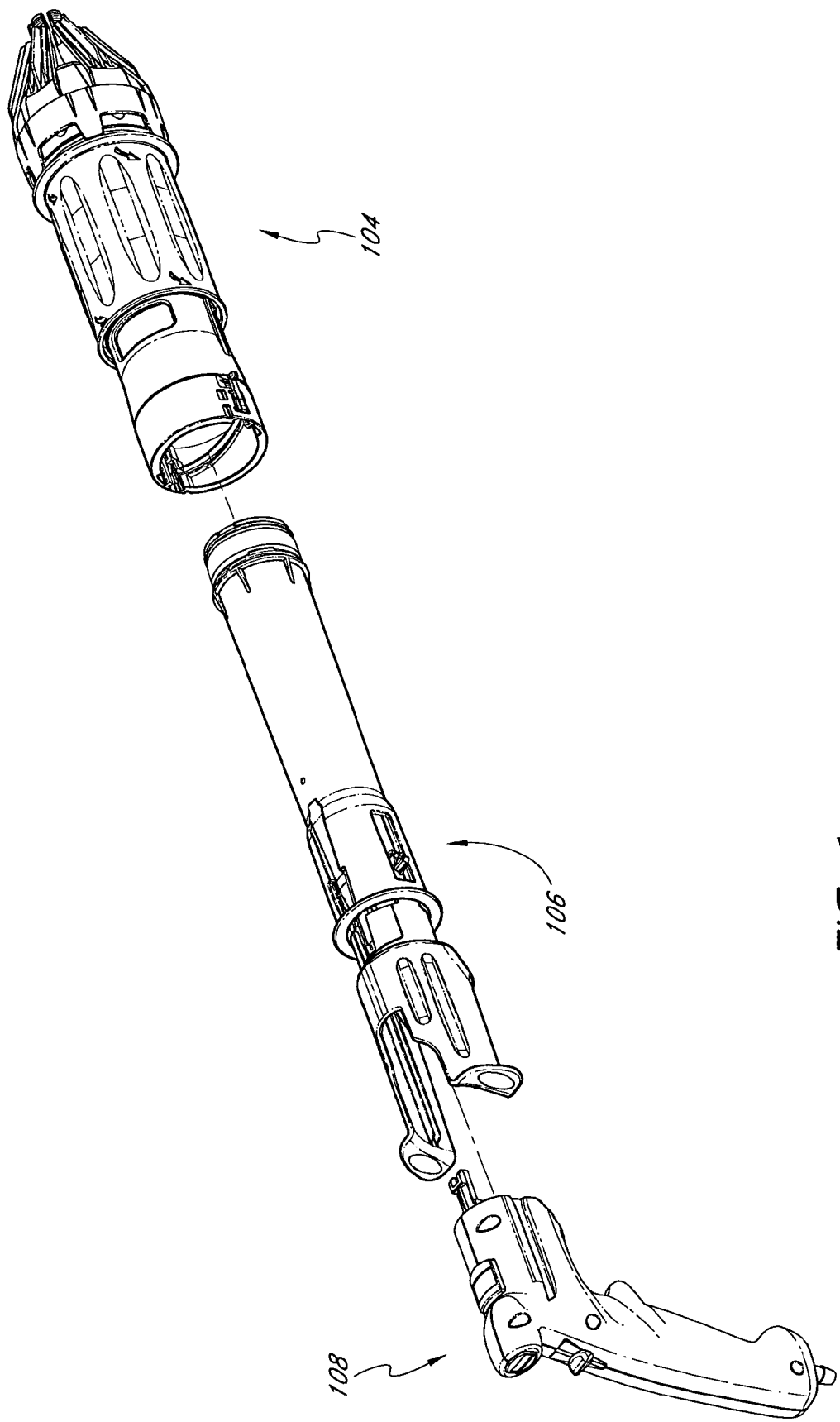
FIG. 1a shows the device of FIG. 1 exploded into 3 components: (1) a loading component; (2) an introducing component; and (3) a handle component.

Key
Full Assembly (FIGS. 1, 1a)
100 Resilient sleeve (FIGS. 1b, 1c)
104 Loading Component (FIG. 2, 2a)
   126 Axis
   110 Retracting Cylinder (FIG. 3)
      114 Retractor (FIG. 8) FIG. 4, 4a, 4b
         117 Gripping Grooves
         118 Thread Tabs
         120 Expander Groove
            122 Wall
            124 Wall
      116 Expander (FIG. 5)
         127 Cylindrical Body
         128 Finger Tabs
            132 Finger Bodies
               136 Support Ribs
            134 Finger Tips
               135 Lateral Bumps
         130 Retractor Tabs
            131 Retractor catch
   112 Guide Cylinder (FIG. 6, 6a)
      140 Operating Cylinder (FIG. 8, 8a, 8b)
         144 External Threads
         146 Securing Recesses
            160 Wall
            161 Wall 162 Wall
163 Wall
148 Locking Grooves
150 Release Channels
151 Loader lock housing (not described!)
138 Finger Tab Guide (FIG. 7, 7a)
152 Protrusions
154 Protrusion Cross-Section
156 Protrusion Edge
158 Protrusion Edge
153 Compression Tabs
142 Loader Locks (FIG. 9, 9a)
166 Loader Lock Button
168 Loader lock groove
170 Loader lock catch
106 Introducing Component (FIG. 11)
192 Axis
174 Retainer (FIG. 12)
178 Proximal Portion (Figure)
186 Proximal Extenders
188 Channel Tabs
187 Lock Notches
190 Proximal Base
192 Distal Cut-out
198 Proximal Upper Cut-out
200 Proximal lower Cut-out
194 Push Ears
196 External Handle Guides
176 Distal Portion (Still need a figure)
182 Distal Extenders
180 Distal Tip
172 Actuator (FIG. 13)
202 Actuating Cylinder (FIG. 14, 14a, 14b, 14c)
210 Longitudinal Slots
212 Locking Tab
214 Tab Ramp
208 Compression Cap
209 Compression Surface
211 Tab Release
213 Compression Groove
215 Wall
217 Wall
204 Locking Cylinder (FIG. 15, 15a, 15b)
220 Handle Tab
218 Raised Grooves
221 Internal Handle Guides
219 Raised Lip
216 Locking Catch
224 Catch Ramp
206 Sleeve Guide
222 Friction Liner (Not described!)
108 Handle Component (FIG. 16c 16a)
226 Handle
228 External Handle Grooves
230 Internal Handle Grooves
232 Lock Release (FIG. 16c)
244 Lock Release Button
246 Lock Release Ramp
234 Handle Release (FIG. 16b)
238 Handle Release Button
240 Handle Catch
242 Latch Spring
Vacuum System
248 Vacuum Source
250 Fitting
254 Vacuum Tubing
252 Vacuum Lever

What is claimed is:

1. A lung resection device for deploying a resilient sleeve around a lung portion, the device comprising:

a. a loading component having a proximal end and a distal end, the loading component comprising:

i. a first cylinder having a plurality of finger tabs at a distal end and a rotatable retractor at a proximal end, the first cylinder configured so as to permit the rotatable retractor to rotate relative to the finger tabs and to permit both said rotatable retractor and said finger tabs to move axially together, said rotatable retractor having a plurality of engagement tabs on the interior surface thereof and a gripping surface on the exterior surface thereof, and ii. a second cylinder positioned concentrically within the first cylinder, the second cylinder having a plurality of finger tab guides at a distal end to guide axial movement of the finger tabs when the rotatable retractor is rotated about said second cylinder, said second cylinder also having helical threads on an external surface thereof in which the engagement tabs of said first cylinder reside, the helical threads configured to guide said rotatable retractor to move proximally and to radially bias said finger tabs away from Axis 126 when said rotatable retractor is rotated, said second cylinder further having securing recesses located at a proximal end of the helical threads that accept therein said engagement tabs when said engagement tabs reach the proximal end of said helical threads to limit relative rotation between said first and second cylinders, said second cylinder also having a plurality of locking grooves of helical shape positioned on an internal surface thereof that extend distally from a proximal end thereof, said second cylinder further having a plurality of release channels located on the internal surface thereof and extending between a distal end of the locking grooves and the proximal end of said second cylinder, said second cylinder further having a plurality of compression tabs on the internal surface of the distal end thereof; and b. an introducing component configured to cooperate with the loading component, the introducing component comprising:

i. a retaining cylinder configured to hold the resilient sleeve in an expanded state at a distal end of the retaining cylinder, said retaining cylinder having a cylindrical shape at a proximal end, the distal and proximal ends separated by a plurality of extensions radially spaced from each other, said retaining cylinder further having a channel tab located on each of the extensions, each channel tab configured to reside and move within the locking grooves and the release channels of the second cylinder of the loading component, ii. a sleeve releaser configured to release the resilient sleeve from the expanded state on to the portion of body tissue, the sleeve releaser comprising:

(a) an actuating cylinder positioned concentrically external to the retaining cylinder, the actuating cylinder having a locking tab at a proximal end thereof, said actuating cylinder also having a plurality of slots at a mid-portion thereof through which the channel tabs of said retaining cylinder protrude thereby preventing relative rotation between said actuating cylinder and said retaining cylinder but permitting relative axial movement therebetween, (b) a locking cylinder located concentrically internal to the retaining cylinder, the locking cylinder having longitudinally oriented channels located on a mid portion of an external surface thereof in which the extensions of the retaining cylinder reside thereby limiting relative rotation between said locking cylinder and said retaining cylinder but permitting relative axial movement therebetween, said locking cylinder having a lock at a mid-portion thereof that is configured to mate with the locking tab of the actuating cylinder, and (c) a sleeve guide comprising resilient material spanning a distal end of the actuating cylinder and a distal end of the locking cylinder, the sleeve guide configured so as to encase the distal end of the retaining cylinder when said retaining cylinder is extended in a distal most position; and iii. a handle releasably connected to the retaining cylinder, the handle having a safety release button configured to release the lock on the locking cylinder from the locking tab on the actuating cylinder;

c. wherein, upon rotation of the rotatable retractor, the channel tabs move within the locking grooves, which causes the loading component to move proximally, which in turn causes the compression tabs to move the actuating cylinder proximally relative to the retaining cylinder, which causes the locking cylinder to move distally, thereby extending said retaining cylinder to its distal most position and engaging the locking tab with the lock and preventing further relative axial movement between said actuating cylinder, locking cylinder, and retaining cylinder, so that the resilient sleeve is positioned for deployment on to the lung tissue.

2. A method of resectioning lung tissue using the resilient sleeve, the method comprising the steps of:
applying the lung resection device of claim 1 to a patient's lung tissue;
drawing a portion of the lung tissue into the resilient sleeve;
releasing the resilient sleeve onto the lung tissue; and
severing a portion of the resilient sleeve and the lung tissue therein.

3. A body tissue resection device for deploying a resilient cylinder around a portion of body tissue, the device compromising:
a first component configured to expand the resilient cylinder by operation of an actuator; and
a second component configured to retain and position said resilient cylinder for deployment on the portion of body tissue;
wherein the first component and the second component are configured such that operation of the actuator expands the resilient cylinder, disposes said resilient cylinder on said second component, and prepares said device to deploy said resilient cylinder,
wherein the first component is rotatably coupled to the second component.

4. The device of claim 3, wherein the resilient cylinder is a sleeve.

5. The device of claim 3, wherein the resilient cylinder is a ligation band.

6. The device of claim 3, wherein the first component comprises a first cylinder that is rotatably coupled to a second cylinder.

7. The device of claim 6, further comprising securing recesses that limit relative rotation between said first cylinder and said second cylinder.

8. The device of claim 3, wherein movement of the first component causes a plurality of compression tabs located at a distal end of said first component to contact a distal end of the second component, thereby limiting relative axial movement between said first component and said second component.

9. The device of claim 3, wherein the second component comprises an inner cylinder and a retaining cylinder that are axially moveable relative to each other.

10. The device of claim 3, wherein the second component comprises a plurality of thumb wings positioned near a proximal end of a handle, the thumb wings being configured to permit an operator to grasp the handle and compress the thumb wings with one hand.

11. The device of claim 3, further comprising a safety button that is located on a handle, the safety button being configured to permit deployment of the resilient cylinder.

12. The device of claim 11, wherein the handle can be grasped and the safety button actuated by a single hand.

13. The device of claim 3, wherein a handle is configured to coupled to a proximal end of the second component.

14. The device of claim 3, wherein at least a portion of an inner surface of the second component is lined with a vinyl mesh configured to reduce friction between the resilient cylinder and the inner surface of the second component.

15. A body tissue resection device for deploying a resilient cylinder around a portion of body tissue, the device compromising:
a loading component configured to expand the resilient cylinder; and
an introducing component moveable with respect to the loading component, the introducing component comprising a first portion and a second portion that are moveable with respect to each other in a first state and are not moveable with respect to each other in a second state;
wherein said loading component and said introducing component are configured such that movement of said loading component with respect to said introducing component expands the resilient cylinder and places the first and second portions in the second state; and
wherein movement of the loading component causes a plurality of compression tabs located at a distal end of said loading component to contact a distal end of the introducing component, thereby limiting relative axial movement between said loading component and said introducing component.

16. The device of claim 15, wherein the resilient cylinder is a sleeve.

17. The device of claim 15, wherein the resilient cylinder is a ligation band.

18. The device of claim 15, wherein the loading component comprises a first cylinder with a plurality of thread tabs that reside within a plurality of threads on a second cylinder.

19. The device of claim 18, wherein movement of the first cylinder causes the thread tabs to reside within a plurality of securing recesses on the second cylinder, thereby limiting relative rotation between said first cylinder and said second cylinder.

20. The device of claim 15, wherein the loading component has a plurality of locking grooves, and the introducing component has a plurality of locking tabs that reside within the locking grooves.

21. The device of claim 20, wherein movement of the loading component causes the locking tabs to reside within a plurality of release channels located on the loading component.

22. The device of claim 21, the first portion of the introducing component comprising:

an inner cylinder having raised guides on an exterior surface thereof; and a retaining cylinder having a plurality of cut-outs in its cylindrical wall at a mid-portion thereof, the remaining portions of the retaining cylinder's cylindrical wall being configured to reside within the raised grooves.

23. The device of claim 22, wherein movement of the loading component causes a distal end of the cut-outs to contact a distal end of the raised grooves, thereby limiting relative axial movement between the inner cylinder and the retaining cylinder.

24. The device of claim 15, wherein the introducing component includes a plurality of thumb wings positioned near a proximal end of a handle configured to allow an operator to comfortably use one hand to grasp the handle and compress the thumb wings.

25. The device of claim 15, wherein a safety button is used to release the first portion and second portion from the second state.

26. The device of claim 25, wherein the safety button is located on a handle.

27. The device of claim 26, wherein the handle can be grasped and the safety button actuated by a single hand.

28. The device of claim 15, further comprising a handle that is configured to couple to a proximal end of the introducing component, the handle having a plurality of guide grooves that are configured to accept therein a plurality of guide tabs located at the proximal end of said introducing component.

29. The device of claim 15, wherein at least a portion of an inner surface of the introducing component is lined with a vinyl mesh configured to reduce friction between the resilient cylinder and the inner surface of the introducing component.

* * * * *

UNITED STATES PATENT AND TRADEMARK OFFICE
CERTIFICATE OF CORRECTION

| | | |
|---|---|---|
| PATENT NO. | : 7,731,651 B2 | Page 1 of 1 |
| APPLICATION NO. | : 11/376780 | |
| DATED | : June 8, 2010 | |
| INVENTOR(S) | : Joseph R. Pearce et al. | |

It is certified that error appears in the above-identified patent and that said Letters Patent is hereby corrected as shown below:

On Title Page (Item 74) Attorney, Line 1, Change "Knobb" to --Knobbe--.

In Column 3, Line 57, After "cylinder" insert --.--.

In Column 4, Line 46, After "15" insert --.--.

In Column 7, Line 63, Change "angled in the towards" to --angled towards--.

In Column 8, Line 62, Change "provided" to --provided.--.

In Column 14, Line 35, Change "outers surface" to --outer surface--.

In Column 16, Line 30 (Approx.), After "106" insert --.--.

In Column 20, Line 12 (Approx.), In Claim 1, after "together" insert --along a longitudinal axis--.

In Column 20, Line 24 (Approx.), In Claim 1, change "Axis 126" to --the longitudinal axis--.

In Column 22, Line 12, In Claim 10, after "compress" insert -- least one of--.

In Column 23, Line 16, In Claim 24, after "compress" insert --at least one of--.

Signed and Sealed this
First Day of February, 2011

David J. Kappos
*Director of the United States Patent and Trademark Office*